US011125752B2

(12) United States Patent
Mir et al.

(10) Patent No.: US 11,125,752 B2
(45) Date of Patent: *Sep. 21, 2021

(54) METHOD FOR RAPID ACCURATE DISPENSING, VISUALIZATION AND ANALYSIS OF SINGLE CELLS

(71) Applicant: Takara Bio USA, Inc., Mountain View, CA (US)

(72) Inventors: Alain-Albert Mir, Redwood City, CA (US); Thomas D. Schaal, San Francisco, CA (US); Chun-Wah Lin, Fremont, CA (US); Shanavaz Loharasp D. Nasarabadi, Fremont, CA (US); Jude Dunne, Menlo Park, CA (US); Maithreyan Srinivasan, Palo Alto, CA (US); Patricio A. Espinoza-Vallejos, Fremont, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/834,569

(22) Filed: Mar. 30, 2020

(65) Prior Publication Data

US 2020/0225236 A1 Jul. 16, 2020

Related U.S. Application Data

(63) Continuation of application No. 15/049,056, filed on Feb. 20, 2016, now Pat. No. 10,641,772.

(60) Provisional application No. 62/118,965, filed on Feb. 20, 2015, provisional application No. 62/147,756, filed on Apr. 15, 2015, provisional application No. 62/237,307, filed on Oct. 5, 2015.

(51) Int. Cl.
| | | |
|---|---|---|
| *G01N 33/574* | (2006.01) | |
| *B01L 3/00* | (2006.01) | |
| *G06T 7/00* | (2017.01) | |
| *C12Q 1/6886* | (2018.01) | |

(52) U.S. Cl.
CPC ...... *G01N 33/57415* (2013.01); *B01L 3/5085* (2013.01); *G01N 33/57492* (2013.01); *G06T 7/0012* (2013.01); *B01L 2300/0829* (2013.01); *B01L 2300/0893* (2013.01); *B01L 2300/0896* (2013.01); *C12Q 1/6886* (2013.01); *C12Q 2600/158* (2013.01); *G01N 2333/82* (2013.01); *G06T 2207/10056* (2013.01); *G06T 2207/30024* (2013.01); *G06T 2207/30242* (2013.01)

(58) Field of Classification Search
CPC ................................................ G01N 33/57415
USPC ......................................................... 506/9
See application file for complete search history.

(56) References Cited

U.S. PATENT DOCUMENTS

| | | |
|---|---|---|
| 5,106,584 A | 4/1992 | Funakubo et al. |
| 5,210,015 A | 5/1993 | Gelfand et al. |
| 5,252,294 A | 10/1993 | Kroy et al. |
| 5,281,516 A | 1/1994 | Stapleton et al. |
| 5,338,671 A | 8/1994 | Scalice et al. |
| 5,342,581 A | 8/1994 | Sanadi |
| 5,475,610 A | 12/1995 | Atwood et al. |
| 5,494,810 A | 2/1996 | Barany et al. |
| 5,496,517 A | 3/1996 | Pfost et al. |
| 5,498,392 A | 3/1996 | Wilding et al. |
| 5,525,300 A | 6/1996 | Danssaert et al. |
| 5,552,321 A | 9/1996 | Focht |
| 5,552,580 A | 9/1996 | Pfost et al. |
| 5,587,128 A | 12/1996 | Wilding et al. |
| 5,589,136 A | 12/1996 | Northup et al. |
| 5,593,838 A | 1/1997 | Zanzucchi et al. |
| 5,602,756 A | 2/1997 | Atwood et al. |
| 5,639,423 A | 6/1997 | Northup et al. |
| 5,656,493 A | 8/1997 | Mullis et al. |
| 5,674,743 A | 10/1997 | Ulmer |
| 5,716,842 A | 2/1998 | Baier et al. |
| 5,720,923 A | 2/1998 | Haff et al. |
| 5,721,136 A | 2/1998 | Finney et al. |
| 5,773,258 A | 6/1998 | Birch et al. |

(Continued)

FOREIGN PATENT DOCUMENTS

| | | |
|---|---|---|
| EP | 0438883 B1 | 5/1996 |
| EP | 0881489 | 12/1996 |

(Continued)

OTHER PUBLICATIONS

Agrawal, S. ed. Methods in Molecular Biology, "Protocols of Oligonucleotides and Analogs," vol. 20, 1993, Cover Pages and Table of Contents, pp. i-xiv (12 pages).

Beier, M. et al. "Versatile Derivatisation of Solid Support Media for Covalent Bonding on DNA-microchips," Nucleic Acids Research. May 1, 1999. vol. 27. No. 9, pp. 1970-1977.

Guschin, D. et al. "Manual Manufacturing of Oligonucleotide, DNA, and Protein Microchips," Analytical Biochemistry. Aug. 1, 1997. vol. 250. No. 2, pp. 203-211.

(Continued)

*Primary Examiner* — Kaijiang Zhang
(74) *Attorney, Agent, or Firm* — Michael J. Blessent; Bret E. Field; Bozicevic, Field & Francis LLP

(57) ABSTRACT

The present disclosure provides methods, device, assemblies, and systems for dispensing and visualizing single cells. For example, provided herein are systems and methods for dispensing a dispense volume into a plurality of wells of a multi-well device, where, on average, a pre-determined number of cells (e.g., 1-20) are present in the dispense volume, and determining, via a cellular label, the number of cells present in each of the plurality of wells. Such dispensing and cell detection may be repeated a number of times with respect to wells identified as having less than the pre-determined number of cells in order increase the number wells in the multi-well device containing the desired number (e.g., a single cell).

18 Claims, 23 Drawing Sheets

(56) References Cited

U.S. PATENT DOCUMENTS

| | | |
|---|---|---|
| 5,779,977 A | 7/1998 | Haff et al. |
| 5,779,981 A | 7/1998 | Danssaert et al. |
| 5,827,480 A | 10/1998 | Haff et al. |
| 5,866,345 A | 2/1999 | Wilding et al. |
| 5,939,312 A | 8/1999 | Baier et al. |
| 5,955,029 A | 9/1999 | Wilding et al. |
| 5,985,555 A | 11/1999 | Bertling |
| 6,015,674 A | 1/2000 | Woudenberg et al. |
| 6,033,880 A | 3/2000 | Haff et al. |
| 6,054,263 A | 4/2000 | Danssaert et al. |
| 6,126,804 A | 10/2000 | Andresen |
| 6,132,580 A | 10/2000 | Mathies et al. |
| 6,153,426 A | 11/2000 | Heimberg et al. |
| 6,171,780 B1 | 1/2001 | Pham et al. |
| 6,174,675 B1 | 1/2001 | Chow et al. |
| 6,184,029 B1 | 2/2001 | Wilding et al. |
| 6,197,572 B1 | 3/2001 | Schneebeli |
| 6,225,061 B1 | 5/2001 | Becker |
| 6,235,471 B1 | 5/2001 | Knapp et al. |
| 6,235,520 B1 | 5/2001 | Malin et al. |
| 6,284,525 B1 | 9/2001 | Mathies et al. |
| 6,303,343 B1 | 10/2001 | Kopf-Sill |
| 6,306,590 B1 | 10/2001 | Mehta et al. |
| 6,309,886 B1 | 10/2001 | Ambrose et al. |
| 6,337,435 B1 | 1/2002 | Chu et al. |
| 6,406,893 B1 | 6/2002 | Knapp et al. |
| 6,420,143 B1 | 7/2002 | Kopf-Sill |
| 6,423,536 B1 | 7/2002 | Javanovich et al. |
| 6,423,948 B1 | 7/2002 | Kwasnoski et al. |
| 6,432,695 B1 | 8/2002 | Zou et al. |
| 6,444,461 B1 | 9/2002 | Knapp et al. |
| 6,448,066 B1 | 9/2002 | Wheatcroft |
| 6,503,750 B1 | 1/2003 | Benett et al. |
| 6,509,186 B1 | 1/2003 | Zou et al. |
| 6,524,532 B1 | 2/2003 | Northup et al. |
| 6,524,830 B2 | 2/2003 | Kopf-Sill |
| 6,537,799 B2 | 3/2003 | Chow et al. |
| 6,541,274 B2 | 4/2003 | Nagel et al. |
| 6,548,263 B1 | 4/2003 | Kapur et al. |
| 6,551,841 B1 | 4/2003 | Wilding et al. |
| 6,576,459 B2 | 6/2003 | Miles et al. |
| 6,586,233 B2 | 7/2003 | Benett et al. |
| 6,602,473 B1 | 8/2003 | Northup et al. |
| 6,605,213 B1 | 8/2003 | Ammann et al. |
| 6,656,724 B1 | 12/2003 | Heimberg et al. |
| 6,657,169 B2 | 12/2003 | Brown et al. |
| 6,660,517 B1 | 12/2003 | Wilding et al. |
| 6,670,153 B2 | 12/2003 | Stern |
| 6,677,151 B2 | 1/2004 | Sandell |
| 6,699,713 B2 | 3/2004 | Benett et al. |
| 6,703,236 B2 | 3/2004 | Atwood et al. |
| 6,730,883 B2 | 4/2004 | Brown |
| 6,756,019 B1 | 6/2004 | Dubrow et al. |
| 6,762,049 B2 | 7/2004 | Zou et al. |
| 6,767,512 B1 | 7/2004 | Lurz et al. |
| 6,814,934 B1 | 11/2004 | Higuchi |
| 6,830,936 B2 | 12/2004 | Anderson et al. |
| 6,875,602 B2 | 4/2005 | Guiterrez |
| 6,962,821 B2 | 11/2005 | Danssaert et al. |
| 7,005,617 B2 | 2/2006 | Brown |
| 7,008,789 B2 | 3/2006 | Gambini et al. |
| 7,030,340 B2 | 4/2006 | Knoche |
| 7,051,536 B1 | 5/2006 | Cohen et al. |
| 7,074,367 B2 | 7/2006 | Lurz et al. |
| 7,133,726 B1 | 11/2006 | Atwood et al. |
| 7,164,077 B2 | 1/2007 | Venkatasubramaniam |
| 7,183,103 B2 | 3/2007 | Gambini et al. |
| 7,238,321 B2 | 7/2007 | Witter et al. |
| 7,311,794 B2 | 12/2007 | Joseph et al. |
| 7,417,726 B2 | 8/2008 | Kao et al. |
| 7,429,479 B2 | 9/2008 | Harding et al. |
| 7,460,223 B2 | 12/2008 | Harding et al. |
| 7,504,241 B2 | 3/2009 | Atwood et al. |
| 7,560,273 B2 | 7/2009 | Sandell |
| 7,611,674 B2 | 11/2009 | Heimberg et al. |
| 7,771,933 B2 | 8/2010 | Arciniegas et al. |
| 9,097,702 B2 | 8/2015 | Fischbach et al. |
| 9,132,427 B2 | 9/2015 | Joseph et al. |
| 9,828,576 B2 | 11/2017 | Viasnoff et al. |
| 2001/0049092 A1 | 12/2001 | Ekins et al. |
| 2001/0055765 A1 | 12/2001 | O'keefe et al. |
| 2002/0030044 A1 | 3/2002 | Brown |
| 2002/0060156 A1 | 5/2002 | Mathies et al. |
| 2002/0068357 A1 | 6/2002 | Mathies et al. |
| 2002/0072112 A1 | 6/2002 | Atwood et al. |
| 2002/0072113 A1 | 6/2002 | Barbera-Guillem et al. |
| 2002/0110899 A1 | 8/2002 | Wheatcroft |
| 2002/0127660 A1 | 9/2002 | Danssaert |
| 2002/0144771 A1 | 10/2002 | Kuczynski |
| 2002/0182544 A1 | 12/2002 | Chan-Park et al. |
| 2003/0006003 A1 | 1/2003 | Matsuoka |
| 2003/0008286 A1 | 1/2003 | Zou et al. |
| 2003/0032191 A1 | 2/2003 | Hilson et al. |
| 2003/0040011 A1 | 2/2003 | Barth et al. |
| 2003/0044324 A1 | 3/2003 | McKlash et al. |
| 2003/0040104 A1 | 7/2003 | Barbera-Guillem |
| 2003/0138829 A1 | 7/2003 | Unger et al. |
| 2003/0138941 A1 | 7/2003 | Gong et al. |
| 2003/0157509 A1 | 8/2003 | Mirzabekov et al. |
| 2003/0199081 A1 | 10/2003 | Wilding et al. |
| 2003/0214994 A1 | 11/2003 | Schicke et al. |
| 2003/0219788 A1 | 11/2003 | Kaltenboeck |
| 2004/0001861 A1 | 1/2004 | Sandell |
| 2004/0029303 A1 | 2/2004 | Hart et al. |
| 2004/0060917 A1 | 4/2004 | LIU et al. |
| 2004/0072334 A1 | 4/2004 | Benett et al. |
| 2004/0096958 A1 | 5/2004 | Pottathil et al. |
| 2004/0123880 A1 | 7/2004 | Chiles et al. |
| 2004/0185504 A1 | 9/2004 | Pantoliano et al. |
| 2004/0209331 A1 | 10/2004 | Ririe |
| 2004/0258568 A1 | 12/2004 | Lurz et al. |
| 2005/0019792 A1 | 1/2005 | McBride et al. |
| 2005/0112634 A1 | 5/2005 | Woudenberg et al. |
| 2005/0129581 A1 | 6/2005 | McBride et al. |
| 2005/0145273 A1 | 7/2005 | Atwood et al. |
| 2005/0176155 A1 | 8/2005 | Klein et al. |
| 2005/0225751 A1 | 10/2005 | Sandell et al. |
| 2005/0233324 A1 | 10/2005 | Corbett et al. |
| 2006/0024831 A1 | 2/2006 | Kao et al. |
| 2006/0027317 A1 | 2/2006 | Joseph et al. |
| 2006/0030035 A1 | 2/2006 | Joseph et al. |
| 2006/0030036 A1 | 2/2006 | Joseph et al. |
| 2006/0030037 A1 | 2/2006 | Joseph et al. |
| 2006/0046304 A1 | 3/2006 | Shigeura et al. |
| 2006/0073491 A1 | 4/2006 | Joseph et al. |
| 2006/0088931 A1 | 4/2006 | Ririe |
| 2006/0094108 A1 | 5/2006 | Yoder |
| 2006/0166226 A1 | 7/2006 | Kudoh et al. |
| 2006/0205064 A1 | 9/2006 | Tajima |
| 2006/0239980 A1 | 10/2006 | Bernad et al. |
| 2006/0246493 A1 | 11/2006 | Jensen et al. |
| 2006/0270026 A1 | 11/2006 | Soh et al. |
| 2007/0084279 A1 | 4/2007 | Huang et al. |
| 2007/0290282 A1 | 12/2007 | Belov et al. |
| 2008/0026483 A1 | 1/2008 | Oldenburg |
| 2008/0176290 A1 | 7/2008 | Joseph et al. |
| 2008/0288179 A1 | 11/2008 | Kao et al. |
| 2008/0299651 A1 | 12/2008 | Atwood et al. |
| 2009/0061513 A1 | 3/2009 | Andersson et al. |
| 2009/0214616 A1 | 8/2009 | Elbert et al. |
| 2010/0056390 A1 | 3/2010 | Fischbach et al. |
| 2010/0233698 A1 | 9/2010 | Joseph et al. |
| 2014/0255276 A1* | 9/2014 | Warrick .................. 422/552 |

FOREIGN PATENT DOCUMENTS

| | | |
|---|---|---|
| EP | 0637999 B1 | 12/1998 |
| EP | 0739423 B1 | 1/2002 |
| EP | 1022059 B1 | 8/2002 |
| EP | 1157744 B1 | 3/2004 |
| EP | 1013342 B1 | 4/2004 |
| EP | 0881950 B1 | 7/2004 |
| EP | 0871545 B1 | 1/2005 |
| EP | 1510823 A2 | 3/2005 |

(56) References Cited

FOREIGN PATENT DOCUMENTS

| | | |
|---|---|---|
| EP | 0733098 B1 | 1/2006 |
| EP | 1539353 B1 | 2/2006 |
| EP | 1510823 A3 | 7/2006 |
| GB | 2370112 A | 6/2002 |
| JP | 2002-010777 A | 1/2002 |
| JP | 2003-014753 A | 1/2003 |
| JP | 3696141 B2 | 9/2005 |
| JP | 2006-223309 A | 8/2006 |
| WO | WO 96/15269 A2 | 5/1996 |
| WO | WO199707390 A1 | 2/1997 |
| WO | WO 97/042500 A1 | 11/1997 |
| WO | WO 2005/028109 A2 | 3/2002 |
| WO | WO 2001/009389 A2 | 2/2003 |
| WO | WO2004013604 A2 | 2/2004 |
| WO | WO 2005/028110 A2 | 3/2005 |
| WO | WO 2005/028629 A2 | 3/2005 |
| WO | WO 2005/028109 A3 | 7/2005 |
| WO | WO 2005/028110 A3 | 8/2005 |
| WO | WO 2005/108604 A2 | 11/2005 |
| WO | WO 2005/028629 A3 | 6/2006 |
| WO | WO 2006/102264 A1 | 9/2006 |
| WO | WO2006127191 A2 | 11/2006 |
| WO | WO 2009/083648 A2 | 7/2009 |
| WO | WO 2009/100933 A1 | 8/2009 |
| WO | WO 2009/083648 A3 | 9/2009 |
| WO | WO 2010022391 A2 | 2/2010 |
| WO | WO-2010022391 A2 * | 2/2010 ............ C12M 41/38 |
| WO | WO 2010/140982 A1 | 12/2010 |

OTHER PUBLICATIONS

Innis et al. "Optimization of PCRs," In: PCR Protocols (Innis, Gelfand, Sninsky and White, eds.). Academic Press, New York. 1990; pp. 3-12.

Joos, B. et al. "Covalent Attachment of Hybridizable Oligonucleotides to Glass Supports," Analytical Biochemistry, Apr. 5, 1997, vol. 247, No. 1, pp. 96-101.

Lin et al. "Fabrication of polydimethylsiloxane (PDMS) pulsating heat pipe," Applied Thermal Engineering. 2009; 29(2-3), pp. 573-580.

McPherson et al. eds. The series Methods in Enzymology (Academic Press, Inc.): PCR 2: A practical approach. Oxford University Press, New York, 1995, 332 pages.

Nagai et al., "High-throughput PCR in silicon based mircochamber array" Biosensors & Bioelectrics 2001, vol. 16, pp. 1015-1019.

Quirk et al. Semiconductor Manufacturing Technology, Prentice Hall, NJ, 2001, 67 pages.

Rychlik et al. "Optimization of the annealing temperature for DNA amplification in vitro," Nucleic Acids Research 1990; 18 (21):6409-6412.

Sambrook et al. Molecular Cloning: A Laboratory Manual, 2nd Edition, 1989, 1546 pages.

Wolf, S. Silicon Processing for the VLSI Era, vol. 1-4, Lattice Press, 2002, 822 pages.

Yoon et al. "Precise temperature and rapid thermal cycling in a micromachined DNA polymerase chain reaction chip" J. Micromech. Microeng. 2002, 12, pp. 813-823.

Bjork (Dissertation, 2014, pp. 1-108).

Gad et al. (Safety Evaluation in the Development of Medical Devices and Combination Products, Third Edition, Chapter 12, 2008, pp. 151-180).

Communication pursuant to Article 94(3) EPC for European patent application No. 08 713 240.3, mailed Mar. 5, 2018, 7 pages.

Communication Extended European search report p for European application No. 16753205.0, dated Jun. 11, 2018, 9. pages.

Collins, et al."The The Poisson 1-15 distribution and beyond: methods for microfluidic droplet production and single cell encapsulation", Lab on a Chip, vaL 15, No. 17, 2015, pp. 3439-3459.

Kachouie, et aL "Arraycount, an algorithm for automatic cell counting in microwell arrays", Biotechniques Rapid Dispatches, Informa Healthcare, US, vaL 47, No. 3, 2009,8 pages.

Kawahara, et al. "High-speed single cell dispensing system", 2011 International Symposium on Micro-NanoMechatronics and Human Science, 2011, 3 pages.

Communication pursuant to Article 94(3) EPC for European application 16753205.0, mailed Mar. 27, 2019.

\* cited by examiner

Adherent neuron U87 MG cellsSuspension neuron U987 lymphocytes cells

Positive control Ab immunostaining of SK-BR-3 Breast cancer cells

Hoechst 33342 "DAPI" filter

Anti-human ERBB2 Ab
(HER2/neu)-APC / Cy5 filter

Negative control: Immunostaining of SK-BR-3 breast cancer cells

Hoechst 33342 "DAPI" filter        Mouse IgG2B-APC / Cy5 filter

Selected Well

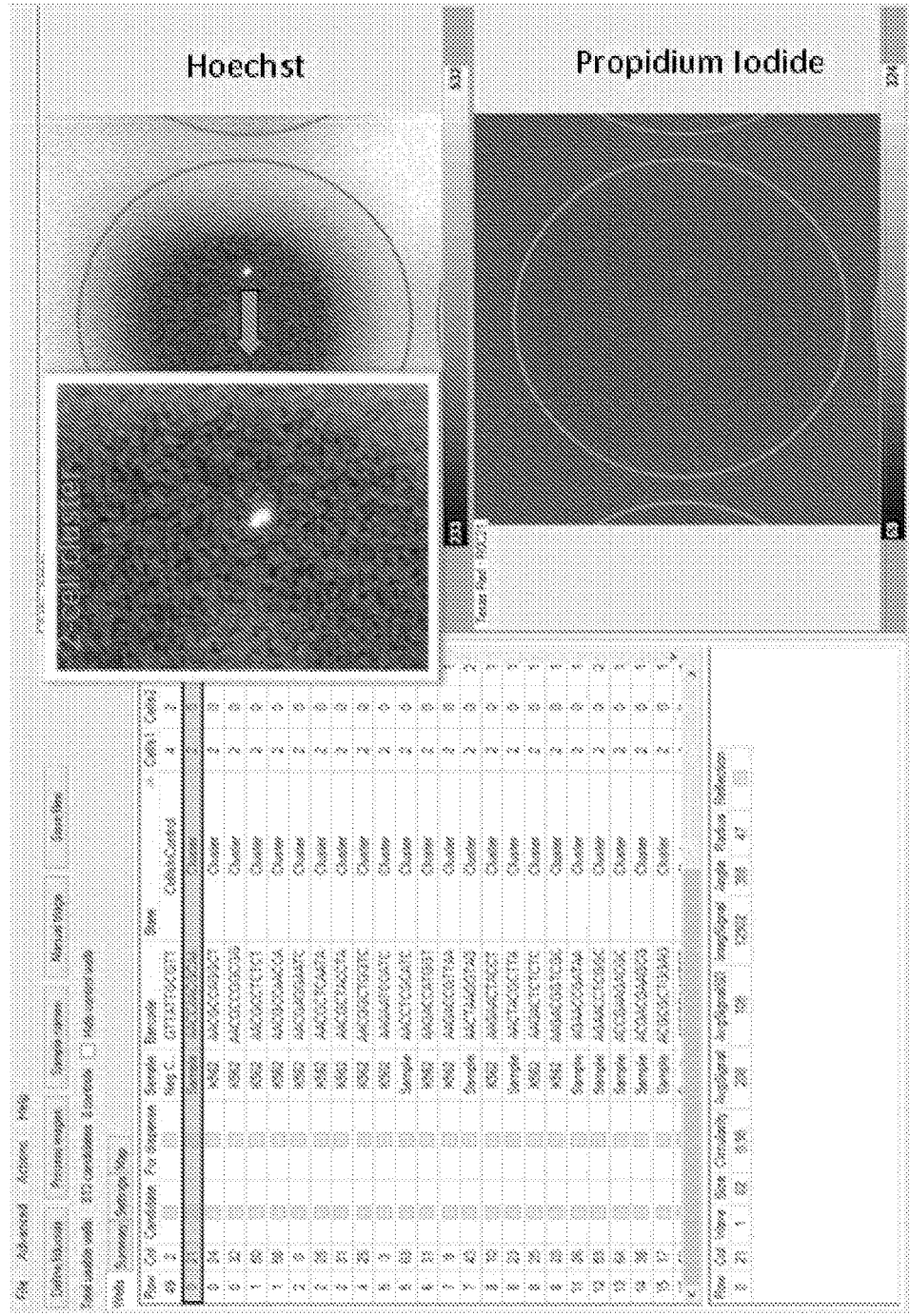
FIG. 18B Rejected Well – 2-cell cluster

Rejected Well – 3-cell cluster

METHOD FOR RAPID ACCURATE DISPENSING, VISUALIZATION AND ANALYSIS OF SINGLE CELLS

The present application claims priority to U.S. provisional application 62/118,965 filed Feb. 20, 2015, U.S. Provisional application 62/147,756 filed Apr. 15, 2015, and U.S. Provisional application 62/237,307 filed Oct. 5, 2015; all of which are herein incorporated by reference in their entireties.

FIELD OF THE DISCLOSURE

The present disclosure provides methods, device, assemblies, and systems for dispensing and visualizing single cells. For example, provided herein are systems and methods for dispensing a dispense volume into a plurality of wells of a multi-well device, where, on average, a pre-determined number of cells (e.g., 1-20) are present in the dispense volume, and determining, via a cellular label, the number of cells present in each of the plurality of wells. Such dispensing and cell detection may be repeated a number of times with respect to wells identified as having less than the pre-determined number of cells in order increase the number wells in the multi-well device containing the desired number (e.g., a single cell).

BACKGROUND

Geneticists are striving to characterize complex diseases like cancer, autoimmune and neurological disorders, but finding the underlying mechanisms driving these diseases has been elusive. Somatic mutations, spontaneous variants that accumulate in cells over a lifetime, are a major factor that drives disease onset and reoccurrence. As cells accumulate new mutations, they form polyclonal cell populations that co-exist with normal cells. Sequencing bulk cell populations can mask the underlying heterogeneity of these unique rare cell types, making it difficult to distinguish them from normal germline mutations. The best way to reveal these differences and visualize the clonal architecture is to sequence individual cells in the population. While single-cell sequencing can help uncover mechanisms of complex disease, traditional approaches are expensive, labor intensive, and require large sample input. What is needed are methods to isolate single cells that, for example, are amenable for use with multi-well devices.

SUMMARY OF THE DISCLOSURE

The present disclosure provides methods, device, assemblies, and systems for dispensing and visualizing single cells. For example, provided herein are systems and methods for dispensing a dispense volume into a plurality of wells of a multi-well device, where, on average, a pre-determined number of cells (e.g., 1-20) are present in the dispense volume, and determining, via a cellular label, the number of cells present in each of the plurality of wells. Such dispensing and cell detection may be repeated a number of times with respect to wells identified as having less than the pre-determined number of cells in order increase the number wells in the multi-well device containing the desired number (e.g., a single cell). In certain embodiments, single-cell analysis (e.g., sequencing) is performed in the wells with a single cell.

Embodiments of the present disclosure provide a method to rapidly select, dispense and visualize and analyze single cells, comprising: a) using a Poisson distribution to dilute and dispense cells at a single cell per well concentration into a plurality of wells of a microfluidic device; and b) visualizing said wells using a microscope and rapid microscope image analysis software to detect, visualize, and select those wells bearing single cells. In some embodiments, the method further comprises the step of performing additional dispense cycles of either cell-containing solutions into individual wells specifically identified as having a cell count of zero (e.g., repeated one or more times) or more than 1 cell. In other embodiments, image analysis and chip mapped positions (e.g., via a dispense map file) direct selection of wells for addition of reagents and materials permitting further biochemical or biophysical and/or cell viability based-investigation.

Further embodiments provide a system, comprising: a) a microfluidic device; and b) a microscope component comprising a microscope and computer software and a computer processor configured to perform rapid microscope image analysis software to detect, visualize, and select wells bearing single cells. In certain embodiments, the system further comprises a dispense map file.

In certain embodiments, the methods further comprise c) dispensing a first reagent into at least one (e.g., 1 . . . 5 . . . 10 . . . 500 . . . 5000 . . . 10,000; all or most wells in multi-well chip) of said selected wells bearing the defined number of cells (e.g., in wells with one and only one cell in a particular well). In some embodiments, the first reagent is selected from the group consisting of: cell culture components, cell health measuring reagents, cell differentiation reagents, drugs, WTA, WGA, nucleic acid, proximity ligation assay (PLA) reagents, cell surface markers, labeled antibodies, unlabeled antibodies, detection reagents associated with antibody detection, nanomaterials, reagents for lysing cells, reagents for detection and/or resolution of nucleic acids or lipids or carbohydrates or protein cell components. In particular embodiments, the defined number of cells per well is 1, or 2, or any number more than 1, or zero.

In certain embodiments, provided herein are methods comprising: a) dispensing a dispense volume of a cell suspension into each of a plurality of wells in a multi-well device, wherein the cell suspension comprises cells present in the cell suspension at a concentration such that, on average, X cell(s) (e.g., 0.1 to 100 cells) is/are present in the dispense volume, and wherein the dispensing is performed with a liquid dispensing system; b) labeling at least a portion of the cells with a first detectable label before and/or after the dispensing; and c) determining the number of cell(s) present in each of at least some of the plurality of wells (e.g., by visualizing stained cells, or sequencing methods).

In some embodiments, X is between 1 and 100 cells (e.g., 1 . . . 5 . . . 10 . . . 15 . . . 20 . . . 30 . . . 40 . . . 50 . . . 60 . . . 70 . . . 80 . . . 90 . . . or 100 cells). In certain embodiments, X is one. In further embodiments, the number of cell(s) in at least one of the plurality of wells is determined to be zero (e.g., at least 20% of the wells result in liquid dispensed, but no cell). In other embodiments, the number of cells in at least one of the plurality of wells is between zero and forty. In further embodiments, the methods further comprise: d) dispensing a dispense volume of the cell suspension into at least some of the wells determined to have less than X cells.

In other embodiments, the methods further comprise: e) dispensing a first additional volume which is approximately equal to the dispense volume, but is free of cells, into at least some of the wells determined to have X cells or more than X cells (e.g., such that the volume of the liquid dispensed into all the wells on a chip remains the same). In other embodiments, the methods further comprise: e) determining the number of cell(s) present in each of the wells previously determined to have less than X cells. In further embodiments, the methods further comprise: f) dispensing a dispense volume of the cell suspension into wells determined to have less than X cells. In other embodiments, the methods further comprise: g) dispensing a second additional volume which is equal to (or about equal to) the dispense volume, but is free of cells, into at least some of the wells determined to have X cells or more than X cells.

In some embodiments, the methods further comprise: labeling at least a portion of the cells with a second detectable label before and/or after the dispensing and/or determining steps. In additional embodiments, the methods further comprise: determining which, if any, of the plurality of wells contain a cell with the second label. In additional embodiments, the determining comprises visualizing the first detectable label in each of the at least some of the plurality of wells. In some embodiments, the determining comprising capturing a first image of at least some of the plurality of wells using an image capturing system, wherein the first image indicates the number of cells present in each of the wells in the first image. In additional embodiments, the image capturing system comprises a camera linked to a magnifying lens. In other embodiments, the image capturing system further comprises a computer, wherein the computer comprises a computer processor, computer memory, and image analysis software. In further embodiments, the image analysis software is configured to analyze the first image and generate: i) a first list of which wells contain less than X cells, ii) a second list of which wells contain X cells; and iii) third list of wells than contain more than X cells. In additional embodiments, the image analysis software generates instructions, for the liquid dispensing system, to dispense a dispense volume into each of the first list of wells. In further embodiments, the methods further comprise: d) dispensing, based on the first image, a dispense volume into at least some of the wells with less than X cells. In other embodiments, the methods further comprise: e) capturing a second image of at least some of the wells with less than X cells prior to the dispensing, wherein the second image indicates, via the first detectable label, the number of cell(s) present in each of the wells with less than X cells prior to the dispensing.

In other embodiments, the liquid dispensing system comprises: i) a plurality of fluidic dispensing channels, ii) a source container containing the cells suspension; and iii) a robotic movement component attached to the fluidic dispensing channels, wherein the robotic movement component is moveable between the source container and the multi-well device. In other embodiments, the liquid dispensing system is automated and is configured to receive instructions from the image analysis software. In some embodiments, the first detectable label comprises a cell stain. In certain embodiments, the first detectable label is selected from the group consisting of: cell culture components, cell health measuring reagents, cell differentiation reagents, drugs, WTA, WGA, nucleic acid, proximity ligation assay (PLA) reagents, cell surface markers, labeled antibodies, unlabeled antibodies, detection reagents associated with antibody detection, nanomaterials, reagents for lysing cells, reagents for detection and/or resolution of nucleic acids or lipids or carbohydrates or protein cell components. In particular embodiments, the cells are epithelial cells, organ cells, skin cells, bacterial cells, human cells, circulating cancer cells, stem cells, hematopoietic stem cells, or any other type of cells.

In certain embodiments, the methods further comprise: d) conducting a biological reaction in at least one of the wells determined to have X cell(s). In other embodiments, the methods further comprise: d) conducting a biological reaction in at least 10% of the wells determined to have X cell(s). In further embodiments, the biological reaction comprises a sequencing reaction. In additional embodiments, the sequencing reaction employs nucleic acid barcode sequences. In further embodiments, the multi-well device comprises at least 30 wells (e.g., 30 . . . 75 . . . 150 . . . 400 . . . 1000 . . . 4,000 . . . 10,000 . . . 20,000 . . . or 30, wells). In other embodiments, the multi-well device comprises at least 1000 wells. In particular embodiments, the multi-well device comprises a multi-well chip (e.g., with nano or micro wells). In other embodiments, the second detectable label is specific for circulating cancer cells and/or cancer stem cells and/or for any other type of target cell desired to be detected. In additional embodiments, the second detectable label comprises an antibody, its conjugate or an antigen binding portion of an antibody.

In certain embodiments, the cells in the cell suspension are purified from tumor or normal tissue. In other embodiments, dispensing volume is between 5 and 9000 nl (e.g., 5 . . . 25 . . . 100 . . . 500 . . . 1000 . . . 4000 . . . 9000 nl). In further embodiments, the labeling the cells is before the dispensing. In additional embodiments, the labeling the cells is after the dispensing.

In certain embodiments, provided herein are systems and kits comprising: a) a multi-well device comprising a plurality of wells; b) a liquid dispensing system configured to dispense a dispense volume into each of the plurality of wells; and c) a cell suspension comprising cells present in the cell suspension at a concentration such that, on average, X cell(s) (e.g., 0.1 to 100 cells) is/are present in the dispense volume.

In other embodiments, X is between 1 and 20 cells (e.g., 1, 2, 3, 4, 5, 6, 7, 8, 9, 10 . . . 15 . . . or 20 cells). In further embodiments, X is one. In particular embodiments, the liquid dispensing system is configured to dispense the dispense volume into each of the plurality of wells in an automated or semi-automated fashion. In other embodiments, the systems further comprise: d) an image capturing system that captures a first image of at least some of the plurality of wells, and determines the number of cells present in each of the wells in the first image. In other embodiments, the image capturing system comprises a camera linked to a magnifying lens. In further embodiments, the image capturing system further comprises a computer, wherein the computer comprises a computer processor, computer memory, and image analysis software. In further embodiments, the image analysis software is configured to analyze the first image and generate: i) a first list of which wells contain less than X cells; and/or ii) a second list of which wells contain X cells; and/or iii) a third list of which wells contain more than X cells. In some embodiments, the image analysis software if configured to generate instructions for the liquid dispensing system to dispense a dispense volume into each of the first list of wells. In other embodiments, the liquid dispensing system comprises: i) a plurality of fluidic dispensing channels, ii) a source container containing the cells suspension; and iii) a robotic movement component attached to the fluidic dispensing channels, wherein the robotic movement component is moveable between the source container and the multi-well device. In additional embodiments, the systems further comprise a first and/or second detectable labels capable of labeling the cells in the cell suspension (e.g., one label to label all of the cells, and another to label cells of interest, such as stem cells or circulating tumor cells). In other embodiments, the cells in the cell suspension are labeled with a first and/or second detectable label. In certain embodiments, the first detectable label comprises a cell stain. In some embodiments, the first detectable label is selected from the group consisting of: cell culture components, cell health measuring reagents, cell differentiation reagents, drugs, WTA, WGA, nucleic acid, proximity ligation assay (PLA) reagents, cell surface markers, labeled antibodies, unlabeled antibodies, detection reagents associated with antibody detection, nanomaterials, reagents for lysing cells, reagents for detection and/or resolution of nucleic acids or lipids or carbohydrates or protein cell components.

In some embodiments, provided herein are methods comprising: a) dispensing a dispense volume of a cell suspension into each of a plurality of wells in a multi-well device, wherein the cell suspension comprises cells present in the cell suspension at a concentration such that, on average, one cell is present in the dispense volume, and wherein the dispensing is performed with a liquid dispensing system; b) labeling the cells with a first detectable label before and/or after the dispensing; and c) determining if zero, one, or multiple (e.g., two, three, four, or more) cells are present in each of at least some of the plurality of wells (e.g., visualizing with a microscope; generating a digital image; or generating computer data; that indicates the number of cells in each well). In certain embodiments, the methods further comprise d) generating a report (e.g., computer code, computer file, written report, or electronic report) that indicates if there is zero, one, or multiple cells in each of the at least some of the plurality of wells. In particular embodiments, the methods further comprise: d) dispensing a dispense volume of the cell suspension into at least one of the wells determined to have zero cells. In other embodiments, the methods further comprise: d) dispensing a dispense volume of the cell suspension into at least 50% (e.g., 50% . . . 67% . . . 75% . . . 85% . . . 95% . . . or 100%) of the wells determined to have zero cells. In other embodiments, the methods further comprise: e) determining if zero, one, or multiple cells are present in each of the wells that were previously determined to have zero cells. In additional embodiments, the methods further comprise: f) dispensing a dispense volume of the cell suspension into wells twice determined to have zero cells. In other embodiments, the methods further comprising: g) determining that at least 50% of all of said plurality of wells present in said multi-well device have a single cell (e.g., at least 50% . . . 55% . . . 60% . . . 65% . . . 75% . . . 80% . . . 85% . . . or 90%).

In some embodiments, the determining comprises visualizing the detectable label in each of the at least some of the plurality of wells. In other embodiments, the determining comprising capturing a first image of at least some of the plurality of wells using an image capturing system, wherein the first image indicates if zero, one, or multiple cells are present in each of the wells in the first image. In other embodiments, the image capturing system comprises a camera linked to a magnifying lens. In further embodiments, the image capturing system further comprises a computer, wherein the computer comprises a computer processor, computer memory, and image analysis software. In additional embodiments, the image analysis software is configured to analyze the first image and generate: i) a first list of which wells contain zero cells and/or ii) a second list of which wells contain one cell. In further embodiments, the image analysis software generates instructions, for the liquid dispensing system, to dispense a dispense volume into each of the first list of wells. In some embodiments, the methods further comprise d) dispensing, based on the first image, a dispense volume into at least some of the wells with zero cells. In additional embodiments, the methods further comprise: e) capturing a second image of at least some of the wells with zero cells prior to the dispensing, wherein the second image indicates, via the first detectable label, if zero, one, or multiple cells are present in each of the wells with zero cells prior to the dispensing. In certain embodiments, methods further comprise centrifuging the multi-well device (e.g., to collect cells in the bottom of each well) prior to the determining step.

In certain embodiments, the liquid dispensing system comprises: i) a plurality of fluidic dispensing channels, ii) a source container containing the cells suspension; and iii) a robotic movement component attached to the fluidic dispensing channels, wherein the robotic movement component is moveable between the source container and the multi-well device. In other embodiments, the liquid dispensing system is automated and is configured to receive instructions from the computer (e.g., from image analysis software). In other embodiments, the first detectable label comprises a cell stain (e.g., Hoechst stain). In other embodiments, the first detectable label is selected from the group consisting of: cell culture components, cell health measuring reagents, cell differentiation reagents, drugs, WTA, WGA, nucleic acid, proximity ligation assay (PLA) reagents, cell surface markers, labeled antibodies, unlabeled antibodies, detection reagents associated with antibody detection, nanomaterials, reagents for lysing cells, reagents for detection and/or resolution of nucleic acids or lipids or carbohydrates or protein cell components. In certain embodiments, the first detectable label is specific for circulating cancer cells and/or stem cells and/or cancer stem cells (e.g., specific for CD44, CD133, ALDH1, etc.).

In some embodiments, the cells are circulating cancer cells. In other embodiments, the cells are stem cells. In further embodiments, the cells are cancer stem cells (e.g., breast CSCs, ovarian CSCs, colon CSCs, prostate CSCs, pancreatic CSCs, etc.). In further embodiments, the methods further comprise: d) conducting a biological reaction in at least one of the wells determined to have a single cell. In other embodiments, the methods further comprise: d) conducting a biological reaction in at least 50% (e.g., at least 50% . . . 70% . . . 90% . . . or 100%) of the wells determined to have one cell. In some embodiments, the biological reaction comprises a sequencing reaction, and/or a PCR reaction, and/or a cell lysis reaction). In particular embodiments, the sequencing reaction employs nucleic acid barcode sequences.

In certain embodiments, the multi-well device comprises at least 50 wells (e.g., 50 . . . 100 . . . 150 . . . 400 . . . 689 . . . 900 . . . or more). In additional embodiments, the multi-well device comprises at least 1000 wells (e.g., 1000 . . . 1500 . . . 2500 . . . 5000 . . . 5184 . . . 10,000 . . . 20,000 . . . or more). In other embodiments, the multi-well device comprises a multi-well chip.

In particular embodiments, the methods further comprise labeling at least some of the cells with a second detectable label before and/or after the dispensing in step a). In certain embodiments, the second detectable label is specific for circulating cancer cells and/or cancer stem cells. In other embodiments, the second detectable label comprises an antibody or an antigen binding portion of an antibody. In some embodiments, the cells in the cell suspension are purified from tumor tissue. In other embodiments, the dispensing volume is between 25 and 500 nl or between 500 nl and 1 ul. In further embodiments, the labeling the cells is before the dispensing. In further embodiments, the labeling the cells is after the dispending.

In some embodiments, provided herein are systems comprising at least two of the following: a) a multi-well device comprising a plurality of wells; b) a liquid dispensing system configured to dispense a dispense volume into each of the plurality of wells; and c) at least one component selected from: i) a cell suspension comprising cells present in said cell suspension at a concentration such that, on average, X cell(s) is/are present in said dispense volume, ii) a dispense map file that provides instructions to said liquid dispensing system for dispensing liquid into cells in said multi-well device that contain X cells.

In certain embodiments, the liquid dispensing system is configured to dispense the dispense volume into each of the plurality of wells in an automated or semi-automated fashion (see, e.g., FIGS. 14-16).

In certain embodiments, the systems further comprise: d) an image capturing system configured to capture a first image of at least some of the plurality of wells, and determine if zero, one, or multiple cells are present in each of the wells in the first image. In other embodiments, the image capturing system comprises a camera linked to a magnifying lens (e.g., a CCD camera linked to microscope optics). In other embodiments, the image capturing system further comprises a computer, wherein the computer comprises a computer processor, computer memory, and image analysis software. In some embodiments, the image analysis software is configured to analyze the first image (and second, third, fourth, etc. images) and generate: i) a first list of which wells contain zero cells and/or ii) a second list of which wells contain one cell. In certain embodiments, the image analysis software if configured to generate instructions for the liquid dispensing system to dispense a dispense volume into each of the first list of wells.

In particular embodiments, the liquid dispensing system comprises: i) a plurality of fluidic dispensing channels, ii) a source container containing the cells suspension; and iii) a robotic movement (e.g., arm) component attached to the fluidic dispensing channels, wherein the robotic movement component is moveable between the source container and the multi-well device.

In some embodiments, the systems further comprise a first and/or second detectable label capable of labeling the cells in the cell suspension. In other embodiments, the cells in the cell suspension are labeled with a first and/or second detectable label. In particular embodiments, the detectable label comprises a cell stain. In some embodiments, the first detectable label is selected from the group consisting of: cell culture components, cell health measuring reagents, cell differentiation reagents, drugs, WTA, WGA, nucleic acid, proximity ligation assay (PLA) reagents, cell surface markers, labeled antibodies, unlabeled antibodies, detection reagents associated with antibody detection, nanomaterials, reagents for lysing cells, reagents for detection and/or resolution of nucleic acids or lipids or carbohydrates or protein cell components.

In certain embodiments, the multi-well device comprises at least 50 wells. In other embodiments, the multi-well device comprises at least 1000 wells. In further embodiments, the multi-well device comprises a multi-well chip. In other embodiments, the systems further comprise a second detectable label that is specific for circulating cancer cells and/or cancer stem cells. In other embodiments, the second detectable label comprises an antibody or an antigen binding portion of an antibody. In certain embodiments, the cells in the cell suspension are purified from tumor tissue. In other embodiments, the dispensing volume is between 25 and 500 nl, or between 50 nl and 1 µl.

DESCRIPTION OF THE FIGURES

FIGS. 18A-E show exemplary output from CellSelect™ image analysis software. In FIG. 18A, a well is presented in row/column position 18/21. Results from this well and its associated images are presented and identify this well as a candidate for inclusion in a dispense file or dispense map. This well contains a single viable cell (indicated by the arrow) illustrating the presence of an object meeting appropriate image analysis thresholds and/or user preferences. In the Hoechst fluorescence image of a single well, (top right panel) there is no obvious corresponding signal in the propidium iodide channel (bottom right panel). FIG. 18B illustrates an example of a well not selected as candidates for inclusion in a dispense map due to analysis resulting in an object being flagged as a potential cell multiplet, cell cluster. FIG. 18C indicates exclusion of well containing greater than 1 cell or exclusion by signal detection in the propodium iodide channel. FIG. 18D illustrates an example of a well that is excluded by the software because it contains three cells. FIG. 18E illustrates a dispense map generated by well selection software. The dispense map is used to program the dispense device to selectively deliver reagents to appropriate wells.

DETAILED DESCRIPTION

Figure 1:
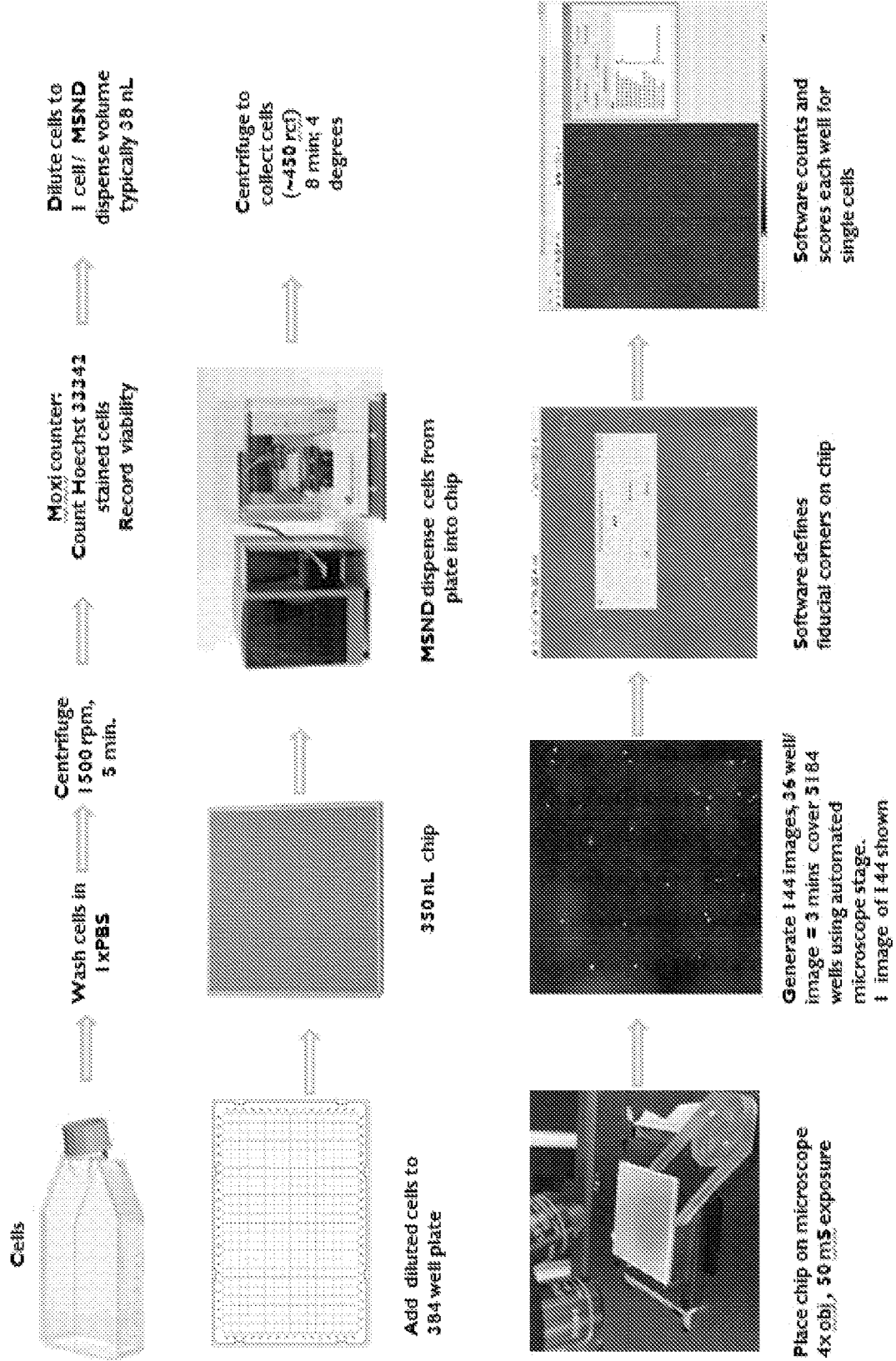
FIG. 1: Flow diagram of the process flow of transferring cells to a chip using an MSND, visualizing by microscopy and selecting cells using Wafergen Celldetector software.

The present disclosure provides methods, device, assemblies, and systems for dispensing and visualizing single cells. For example, provided herein are systems and methods for dispensing a dispense volume into a plurality of wells of a multi-well device, where, on average, a pre-determined number of cells (e.g., 1-20) are present in the dispense volume, and determining, via a cellular label, the number of cells present in each of the plurality of wells. Such dispensing and cell detection may be repeated a number of times with respect to wells identified as having less than the pre-determined number of cells in order increase the number wells in the multi-well device containing the desired number (e.g., a single cell). In certain embodiments, single-cell analysis (e.g., sequencing) is performed in the wells with a single cell. Cell heterogeneity is a general feature of biological tissues and cells in general.

Geneticists are striving to characterize complex diseases including cancer, autoimmune and neurological disorders. However, determining the underlying mechanisms driving these diseases remains elusive. As cells accumulate new mutations, they may form polyclonal cell populations that co-exist with normal cells. As a consequence, sequencing bulk cell populations can mask the underlying heterogeneity of these unique rare cell types, rendering it difficult to "find needles in the haystack." An alternate approach to reveal intra-population/inter-cell differences is to assess the nucleic acid sequences in selected individual cells from a population. Single-cell analyses have been used to define subpopulations with distinct DNA and RNA expression profiles. In summary, it is widely believed that single-cell analysis may uncover previously "hidden" mechanisms of complex disease.

A core requirement in the single-cell field is to clearly and unambiguously detect that the sample being assessed only contains a single cell. Traditional single cell isolation approaches including: FACS instrumentation (Becton Dickinson) microfluidic capture (Fluidigm) limited or widely dispersed cell dilution methods are too expensive, labor intensive, require large sample input methods, and do not readily scale into the need for more cells within standard molecular biology workflows. On the other hand, random deposition of cells may be unpredictable/stochastically distributed, making predictions of cell distributions unwieldy.

An alternate approach is to dispense cells into reaction chambers such that the average over many such dispenses results in a single cell being dispensed. A statistical description of this phenomenon is known as the Poisson distribution. In theory, dispensing a single cell per well (n=exactly 1 cell, but not 0, 2, 3, 4, 5, 6 etc cells) is constrained by theta theoretical maxima=of 36.8% of wells will contain exactly 1 cell. However, the Poisson distribution however can be leveraged to alter the input cell concentration to a very wide range of occupancy rates. A tradeoff in optimizing for a desired number of cells per well (i.e., 1 cell/well) exists. More specifically, optimizing to achieve a desired ratio (10:1 ratio where lambda approaches 0.185) of wells containing a single cell may result in an unsatisfactory percentage of wells without any cells (>82%). A similar approach attempting to specifically target 1 cell per well alongside a size separation approach has recently been reported. However, in that case, possibly due to the physical constraints in the cell capture device employed, only 10% of wells contained single cells. However, that methodology is complex and requires specialized reagents. In that case, possibly due to physical constraints of that system, only 10% of wells contained single cells. Critically, the size constriction component of such devices cannot exclude the possibility that each well contains only a single cell.

Emulsion-based methods, for selecting single cells include placing cells in water-in-oil emulsions. Such systems offer the advantage of insulating against cross contamination. However, these oil-separated compartments are difficult to manipulate. Moreover, such emulsions often require vortexing that depend on standard unselected Poisson statistics to achieve clonality. However, these approaches lead to only a small fraction of occupied and a large number of unoccupied compartments. As a consequence, emulsions are generated in microfluidic systems which increase cost and bear the significant disadvantage that once an emulsion is formed, it is difficult to exchange additional material in wells in a controlled fashion. Moreover, emulsion PCR is optionally performed using conditions that are not easily generalizable.

It is difficult to isolate single cells without expensive and complicated equipment. Moreover, such system cannot typically capture more than 384 single cells. As a result, provided herein are statistical methods combined with microscopy to visualize the cells in microfluidic chips (e.g., those sold by Wafergen, Freemont, Calif.). Work conducted during the development of embodiments of the present disclosure employed the Poisson distribution to dispense cells, and solves a problem associated with a Poisson distribution. In brief, the Poisson distribution is statistically limiting (Table 1) for dispensing single cells because the microchip will either have far too many wells with zero cells (vast underutilization of chip capacity) or too many wells with two or more cells (undermining and confounding the "single-cell" analysis).

TABLE 1

Poisson Distribution Percentages of Cell Counts (n = 0, n = 1, n > 1) at Different Lambda Values

| | Lambda Value | Percentage of Cell Counts = 0 | Percentage of Cell Counts = 1 | Percentage of Cell Counts > 1 | Ratio of "Counts Equal to 1.0" to "Counts > 1.0": | Projected Single Cells Dispensed into 5,184-well chip |
|---|---|---|---|---|---|---|
| 1 | 0.100 | 90.5% | 9.0% | 0.5% | 19.3 | 469 |
| 2 | 0.185 | 83.1% | 15.4% | 1.5% | 10.2 | 797 |
| 3 | 0.200 | 81.9% | 16.4% | 1.8% | 9.3 | 849 |
| 4 | 0.300 | 74.1% | 22.2% | 3.7% | 6.0 | 1152 |
| 5 | 0.400 | 67.0% | 26.8% | 6.2% | 4.4 | 1390 |
| 6 | 0.500 | 60.7% | 30.3% | 9.0% | 3.4 | 1572 |
| 7 | 0.600 | 54.9% | 32.9% | 12.2% | 2.7 | 1707 |
| 8 | 0.700 | 49.7% | 34.8% | 15.6% | 2.2 | 1802 |
| 9 | 0.800 | 44.9% | 35.9% | 19.1% | 1.9 | 1863 |
| 10 | 0.900 | 40.7% | 36.6% | 22.8% | 1.6 | 1897 |
| 11 | 1.000 | 36.8% | 36.8% | 26.4% | 1.4 | 1907 |
| 12 | 1.100 | 33.3% | 36.6% | 30.1% | 1.2 | 1898 |
| 13 | 1.200 | 30.1% | 36.1% | 33.7% | 1.1 | 1874 |
| 14 | 1.300 | 27.3% | 35.4% | 37.3% | 0.9 | 1837 |

TABLE 1-continued

Poisson Distribution Percentages of Cell Counts (n = 0, n = 1, n > 1) at Different Lambda Values

| | Lambda Value | Percentage of Cell Counts = 0 | Percentage of Cell Counts = 1 | Percentage of Cell Counts > 1 | Ratio of "Counts Equal to 1.0" to "Counts > 1.0": | Projected Single Cells Dispensed into 5,184- well chip |
|---|---|---|---|---|---|---|
| 15 | 1.400 | 24.7% | 34.5% | 40.8% | 0.8 | 1790 |
| 16 | 1.500 | 22.3% | 33.5% | 44.2% | 0.8 | 1735 |
| 17 | 1.600 | 20.2% | 32.3% | 47.5% | 0.7 | 1675 |
| 18 | 1.700 | 18.3% | 31.1% | 50.7% | 0.6 | 1610 |
| 19 | 1.800 | 16.5% | 29.8% | 53.7% | 0.6 | 1542 |
| 20 | 1.900 | 15.0% | 28.4% | 56.6% | 0.5 | 1473 |
| 21 | 2.000 | 13.5% | 27.1% | 59.4% | 0.5 | 1403 |

Lambda (λ): mean number of occurrences over a continuous span of time or distance This disclosure overcomes the statistical limitations of technologies that have, for example, (a) only a single dispense opportunity at their disposal, and/or, (b) no visual confirmation of which wells actually contain single cells. In some embodiments, it is established with 99% confidence (or greater) that the samples submitted for downstream genomic or other analysis contain one and only one cell. The present disclosure provides, in certain embodiments, a simple, robust commercially applicable method that employs Poisson statistics, robotic liquid handling and microscopy based image analysis (e.g., in combination with software) in an iterative manner to rapidly and accurately identify single cells in wells of a multi-well device (e.g., >2,000 or more single cells per chip in a 5,184 well format). Such methods are scalable to larger numbers as desired. Solving this problem has considerable commercial, scientific and ultimately medical value.

Figure 14:
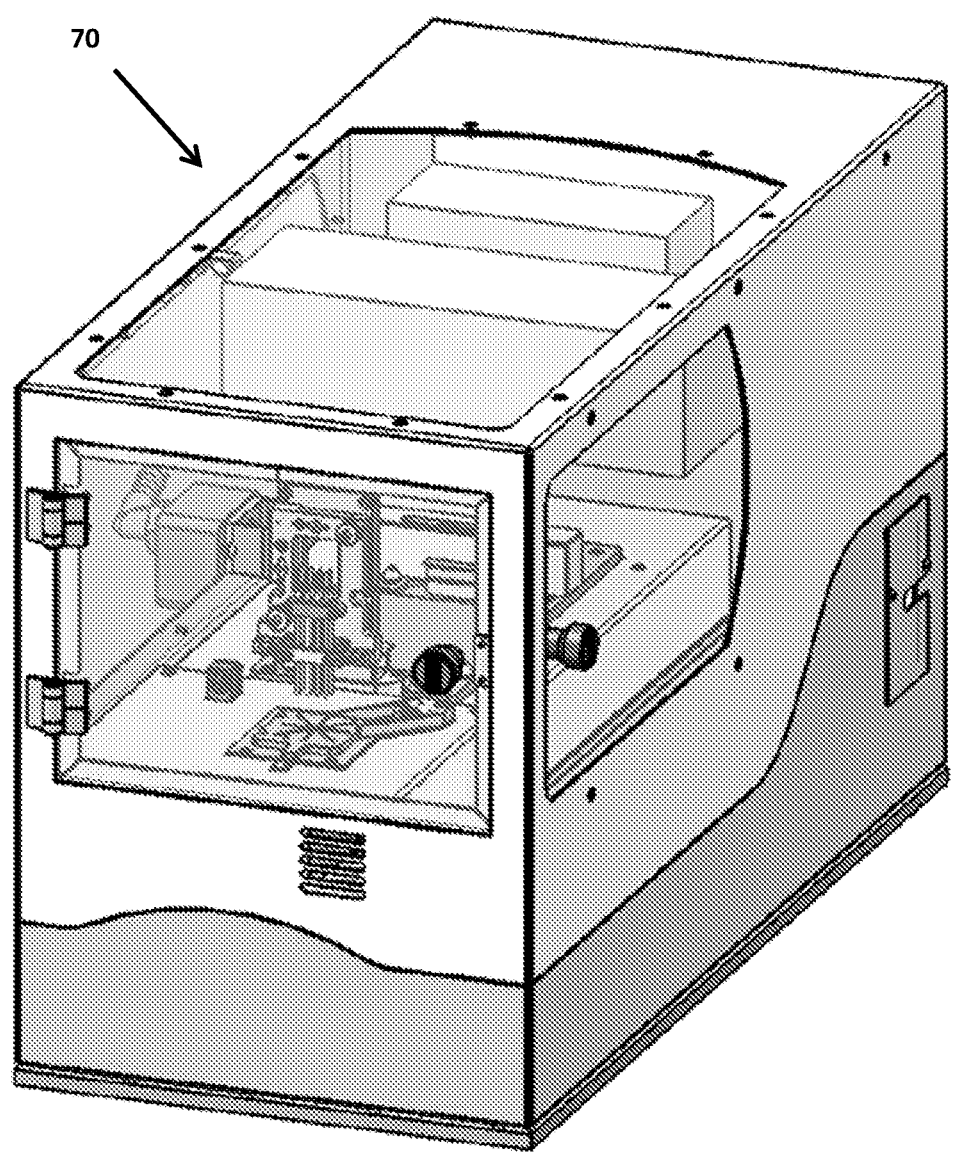
FIG. 14 shows an exemplary robotic liquid dispensing system (70) enclosed in a hood.
Figure 15:
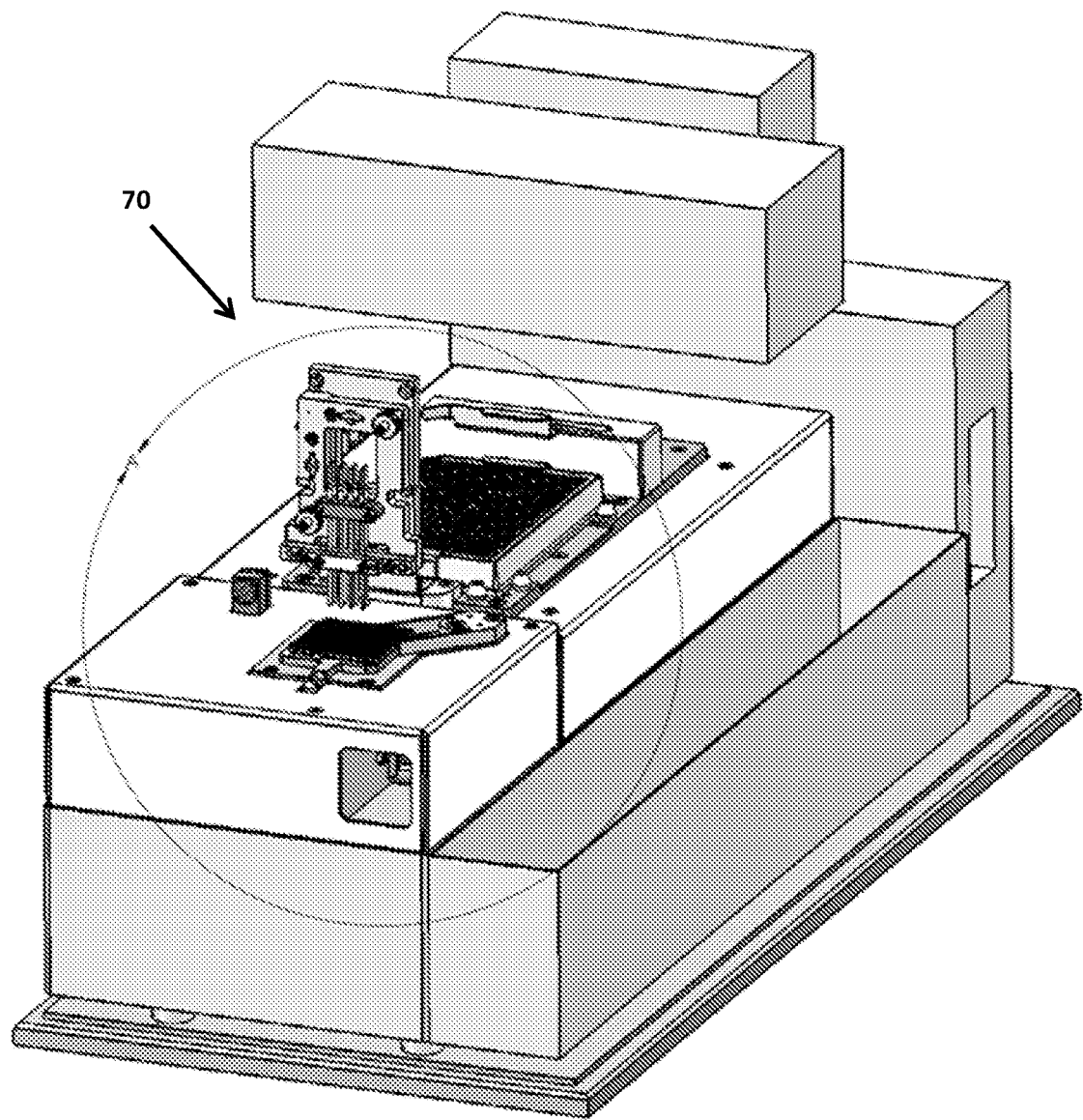
FIG. 15 shows an exemplary robotic liquid dispensing system (70) with the hood removed.
Figure 16:
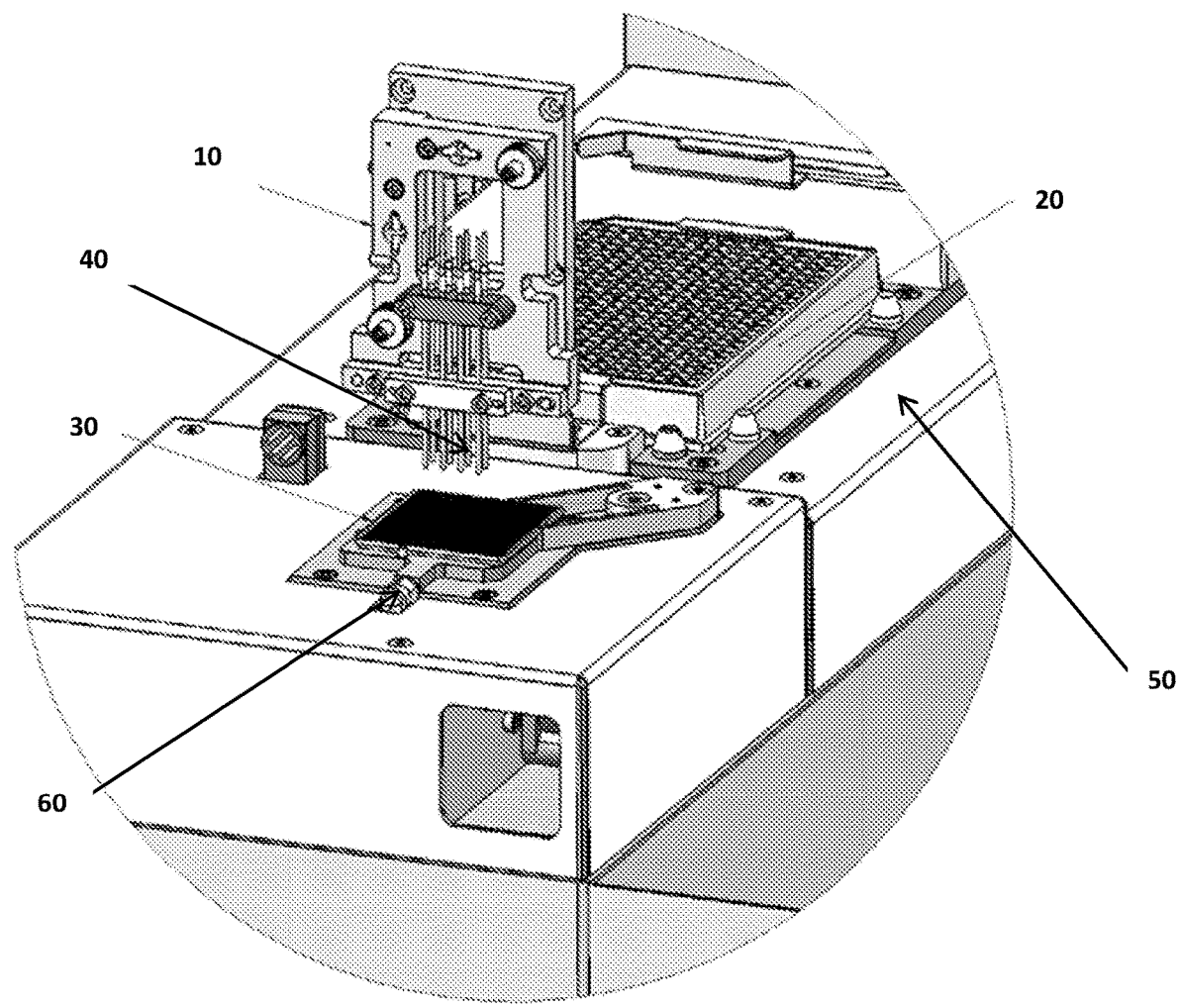
FIG. 16 shows a close up view of an exemplary robotic liquid dispensing system, including: a fluid movement component (10) which contains a plurality of fluidic channels (40); a source container (20) shown with 384 individual sample source compartments and a first securing component (50) for holding the source container (20) in place; and a multi-well testing device (30), which may be WAFERGEN's 5184-nanowell chip, which is secured in place by a second securing component (60).

This disclosure describes the use of microfluidic (e.g., WaferGen SmartChip) technology to isolate and process single cells for either DNA, RNA, and/or other applications. Cells are diluted using Poisson statistics such that on average 1 cell per dispense volume is dispensed. In certain embodiments, microscopy (e.g., magnifying optics) is used to visualize each well and directly know if that well contains a single cell. In certain embodiments, multisample dispensers (e.g., as shown in FIGS. 14-16) are programmed to perform a variety series of biochemical steps including lysis, DNA or RNA amplification, and sample barcoding specifically in wells only bearing a single cell. Examples of the analysis that can be performed include WGA, PCR or Next Generation Sequencing.

In certain embodiments, when wells are identified as having received zero cells, a second (and third) optional Recursive Poisson Distribution (RPD) step may be employed to circumvent the statistical limitations of the Poisson distribution, thereby raising single cell occupancy rates on-chip from a theoretical maxima of 37% to >50%. The RPD in this disclosure refers to the iterative cycle of, (a) dispensing cell-containing solutions into reaction vessels (wells, chambers, etc.) in a chip, (b) visualization of cells on-chip in individual wells, (c) identifying the on-chip cell counts (equal to zero, equal to one, and greater than one) in individual wells by software-aided microscopy, and, (d) performing additional dispense cycles of cell-containing solutions into individual wells specifically identified in the previous round as having a cell count of zero. The objective of RPD is to maximize the number of occupied reaction vessels (wells, chambers, etc.) containing a single-cell (or some other desired number of cells) above the theoretical limitations Poisson distribution for a single dispense. This disclosure does not place a limit on the number of iterative cycles.

In summary, the utility, straight forward nature and robustness of this approach commend it for use, for example, in a variety of situations where commercially relevant R&D, screening, compound analysis, and/or diagnostics on single cell nucleic acids are to be performed.

In some embodiments, this disclosure describes methods of isolating individual cells and transferring them into individual wells of microfluidic (e.g., Wafergen's SmartChip wells). For example, cells are first stained with the commonly available supravital dye Hoechst 33342 that emits a strong blue fluorescence when bound to DNA. The cells are counted, diluted to contain 1 cell per dispense volume, added to a source container (e.g. 384 well plate) and dispensed directly into a deep-well chip using a robotic micro-liquid dispenser (e.g., Wafergen Multiple Sample Nano Dispenser (MSND)). The multi-well chip is centrifuged to collect cells in the bottom of each well. Each well is then visualized by automated microscopy and image analysis to categorically confirm if either 0, 1, 2, 3 or 4 cells are dispensed in each well. This quality control step is both important and unique as it rapidly and definitively identifies the contents of wells in each of the wells in the chip. This exemplary process is illustrated in FIG. 1.

Figure 2:
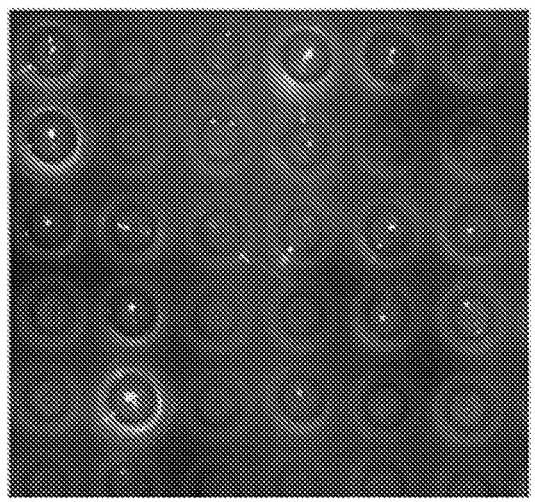
FIG. 2: A 4× objective microscope field of view of both adherent (trypsinised) U87 MG neuronal cells and suspension U937 lymphocytes is visualized, respectively, in a 350 nL deep-well chip. Single cells are readily identified as bright dots within the chip wells
Figure 2:
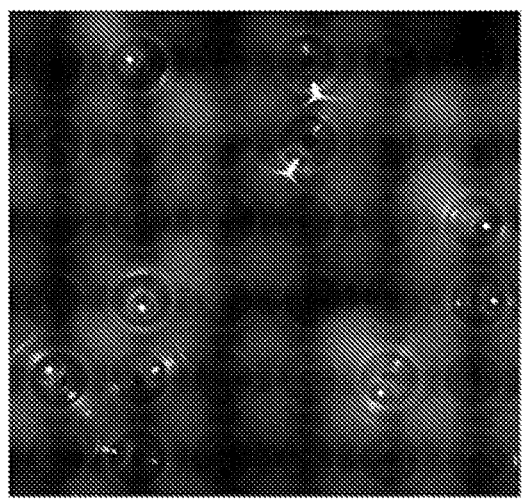

FIG. 2 illustrates a 4× objective microscope view of adherent (trypsinised) U87-MG neuron cells (panel 1) and suspension U937 lymphocytes (panel 2) visualized in a deep well. FIG. 2 illustrates the capacity of this system to dispense either adherent or suspension culture cells. This process takes ~10 minutes to dispense cells into a 5184 well chip and 3 minutes to microscopically image. Dispensed cells can, for example, be used directly or frozen at −80° C. until convenient for downstream analysis. The cells visualized in this chip were prepared as described in FIG. 1.

Figure 3:
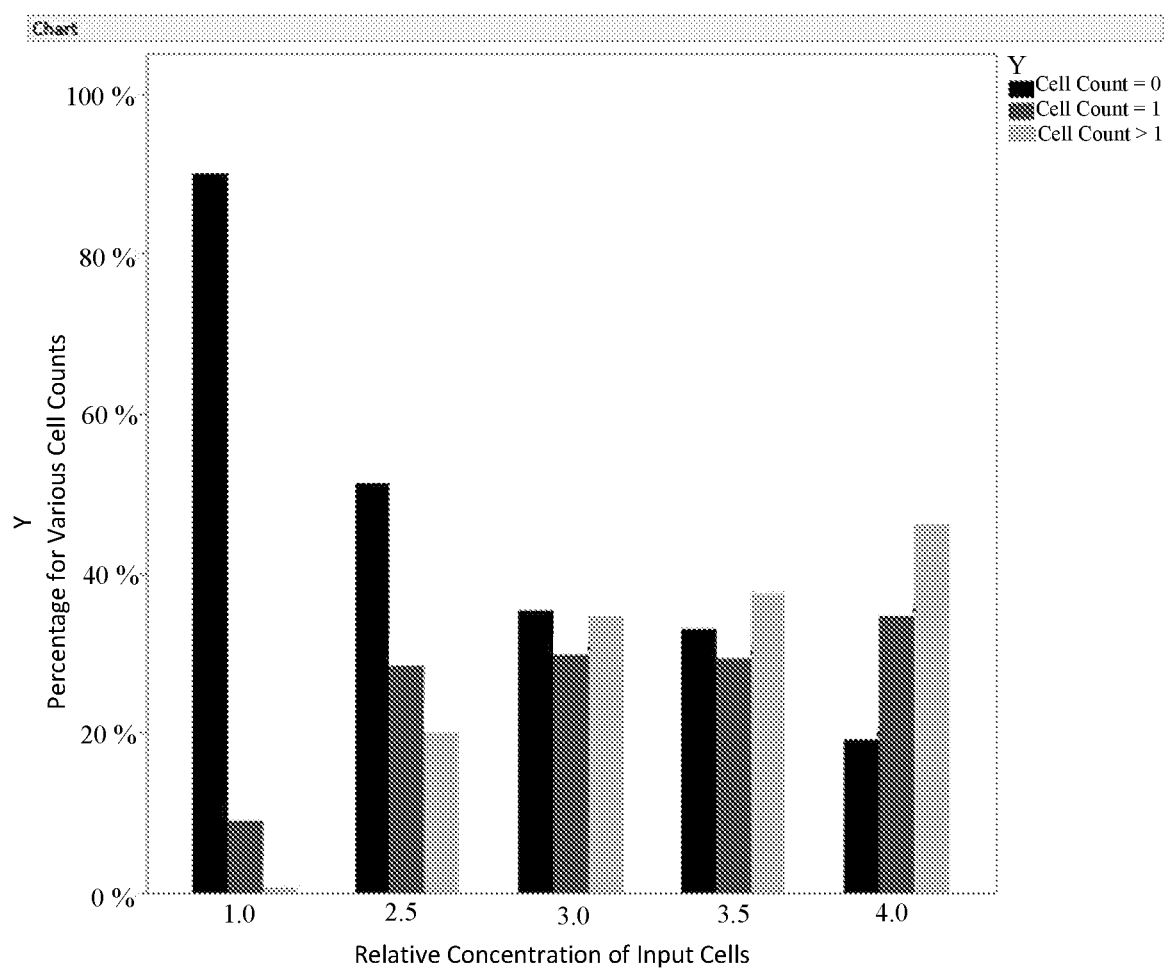
FIG. 3: The bar graph indicates the relative cell counts from an on-chip dispense experiment using deep-well Wafergen chip. The relative percentages of cell counts equal to zero, equal to one and greater than one are shown as a function of increasing relative concentration of the input: cultured U937 cells stained with Hoechst 33342 (compare to theoretical percentages in Table 1). Seven fields of view (FOVs, typically 36 wells per FOV) were analyzed for each concentration of input cells by manually counting following imaging using UV excitation. The "Cell Counts=0", "Cell Counts=1" and "Cell Counts >1" are shown in black, dark gray and light gray, respectively, for each relative concentration of input cells on the chart.

In word conducted during development of embodiments of the present disclosure, it was routinely observed that between 14% and 29% of a 5184 well chip (n=5 chips seeded with different concentrations of cells) had single cells. These single cell occupancy rates convert to between 725 to 1451 single cells in a single 5184 well chip. Those occupancy rates are between 7 and 15 times higher than the single cell market leader (Fluidigm) single cell 96 cell recovery rates. An experiment was performed in which the input cells were titrated across a four-fold relative concentration range in order to assess the "on-chip" cell count distribution profile following a single dispense using the MSND (FIG. 3; Table 2).

TABLE 2

| Relative Concentration of Input Cells | Cell Count = 0 | Cell Count = 1 | Cell Count > 1 |
|---|---|---|---|
| 1 | 1.0 | 90.1% | 9.1% | 0.8% |
| 2 | 2.5 | 51.2% | 28.6% | 20.2% |
| 3 | 3.0 | 35.5% | 29.8% | 34.7% |
| 4 | 3.5 | 33.1% | 29.5% | 37.5% |
| 5 | 4.0 | 19.1% | 34.7% | 46.2% |

In this study, the single cell count was 29.8% for the cell concentration at the apparent maxima (e.g., for the Relative Concentration of Input Cells=3.0). Overall, the relative distributions of cell counts (e.g., equal to zero, equal to one, and greater than one) over the input cell concentration range examined adequately mirror a Poisson distribution (see Table 1). In certain embodiments, the methods and systems of the present disclosure have the benefit of being relatively straight forward to perform, and highly robust with minimal training. The disclosure offers numerous advantages relative to current single cell isolation approaches, removing the need for complex and expensive low throughput microfluidics system (e.g., Fluidigm C1 chip) and elimination of excessive physical manipulation of the cells (FACS). It has the benefit of being an open system such that a variety of Biochemical and Molecular Biology protocols can be performed in these wells. Emulsion PCR is not necessary. Moreover, it isolates significantly more single cells than other systems with minimal training or equipment required. In certain embodiments, performing one or more recursive Poisson distribution step(s) is contemplated to circumvent the statistical limitations (Table 1) of the Poisson distribution raising single cell occupancy rates to, for example, greater than 50% (e.g., greater than 50% . . . 60% . . . 75% . . . 85% . . . or more).

Figure 4:
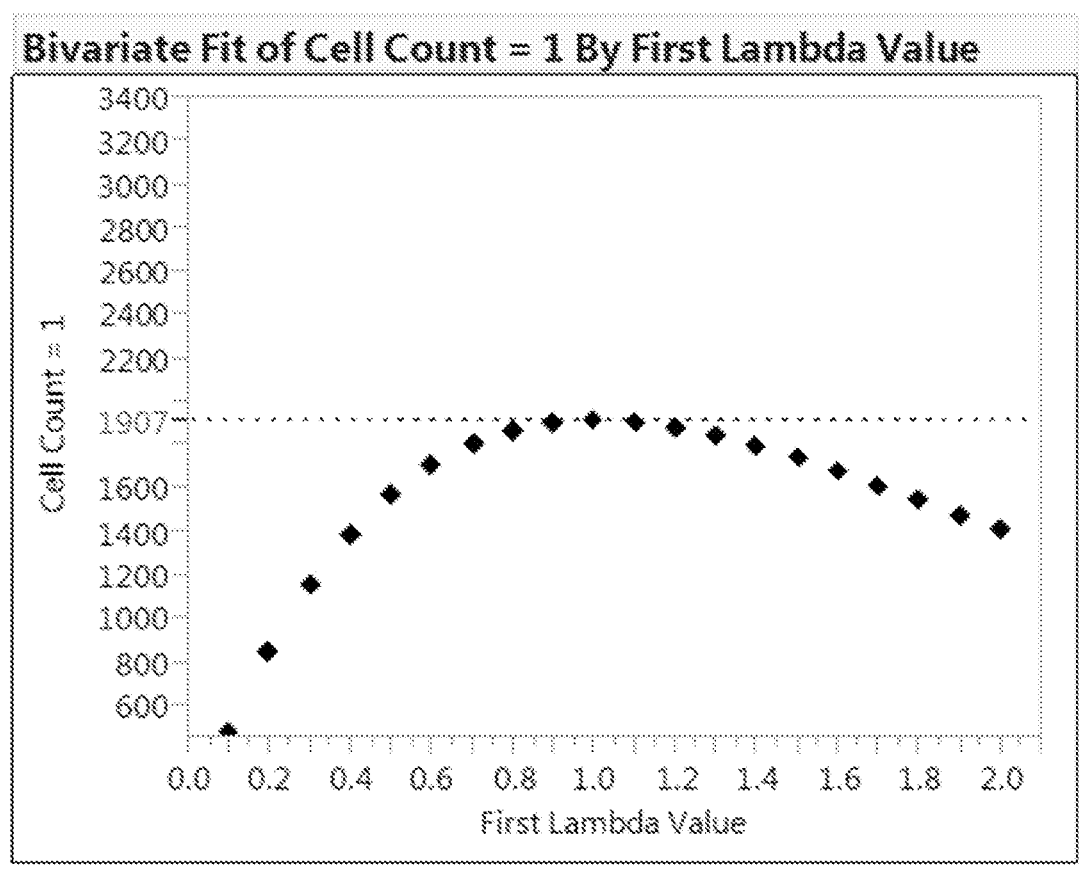
FIG. 4: Theoretical curve fit for an idealized Poisson distribution of cells into the 5,184 well chip format (72×72 format) are shown for the case of using only one Poisson-distributed dispense step. The number of theoretical wells containing a single cell per well after the first dispense are shown as a function of the first lambda (mean) value. The data points for this initial dispense are shown as black diamonds in this graph as well as the subsequent graphs in FIGS. 5-9.
Figure 5:
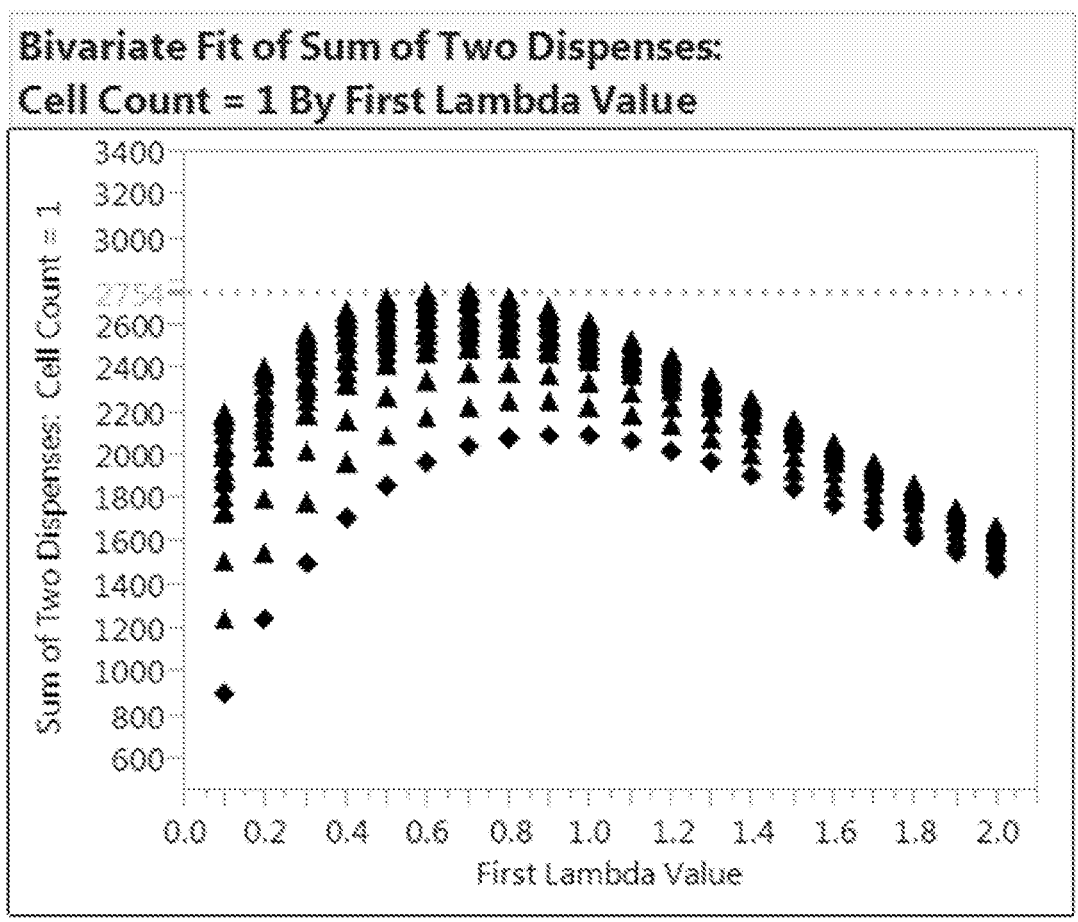
FIG. 5: Theoretical curve fit for an idealized Poisson distribution of cells into the 5,184 well chip format (72×72 format) are shown for the case of using two dispense steps. Here, the number of remaining wells predicted to contain zero cells subsequent to first dispense are identified and subjected to a second MSND Poisson-distributed dispense (Recursive Poisson Distribution; RPD). The number of theoretical wells containing a single cell per well after the second dispense are shown as a function of the first lambda (mean) value. The data points for this two dispense format are shown as black circles in this graph as well as the subsequent graphs in FIGS. 6-9.
Figure 6:
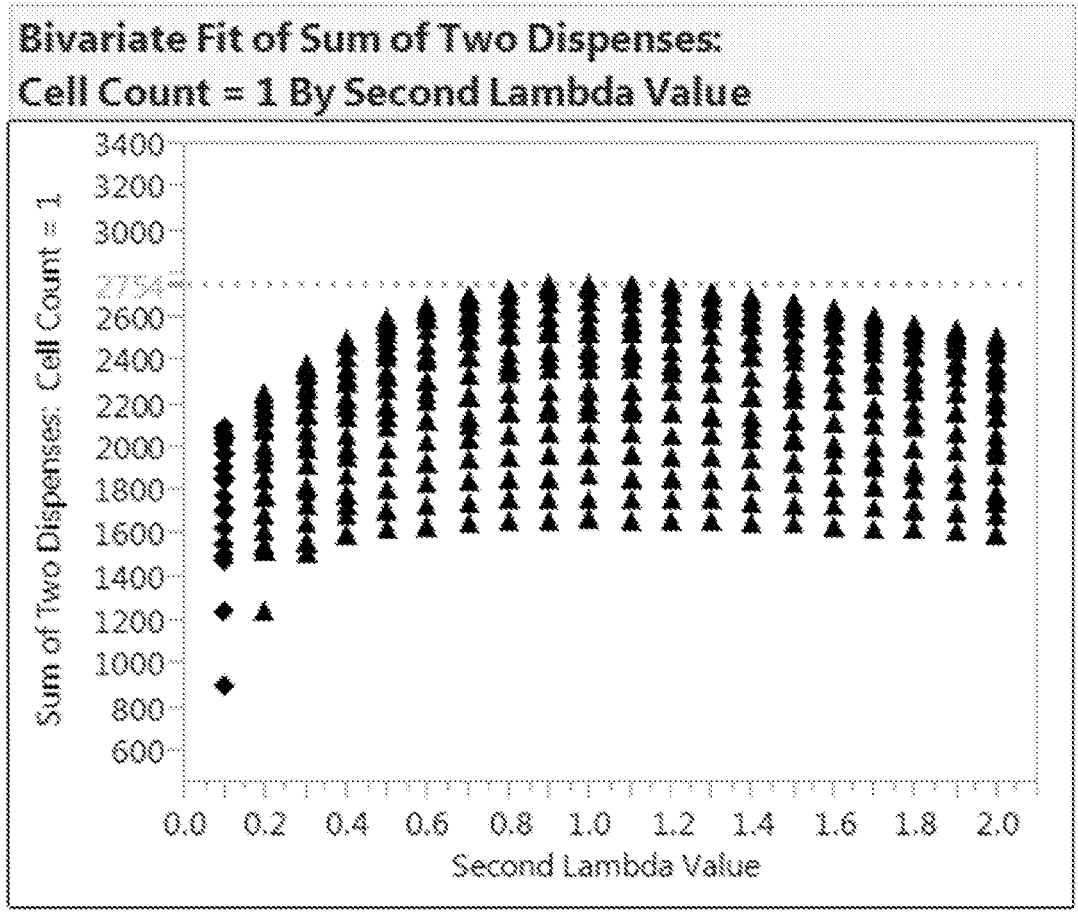
FIG. 6: Theoretical curve fit for an idealized Poisson distribution of cells into the 5,184 well chip format (72×72 format) are shown for the case of using two dispense steps. Here, the number of remaining wells predicted to contain zero cells subsequent to first dispense are identified and subjected to a second MSND Poisson-distributed dispense (RPD). The number of theoretical wells containing a single cell per well after the second dispense are shown as a function of the second lambda (mean) value.
Figure 7:
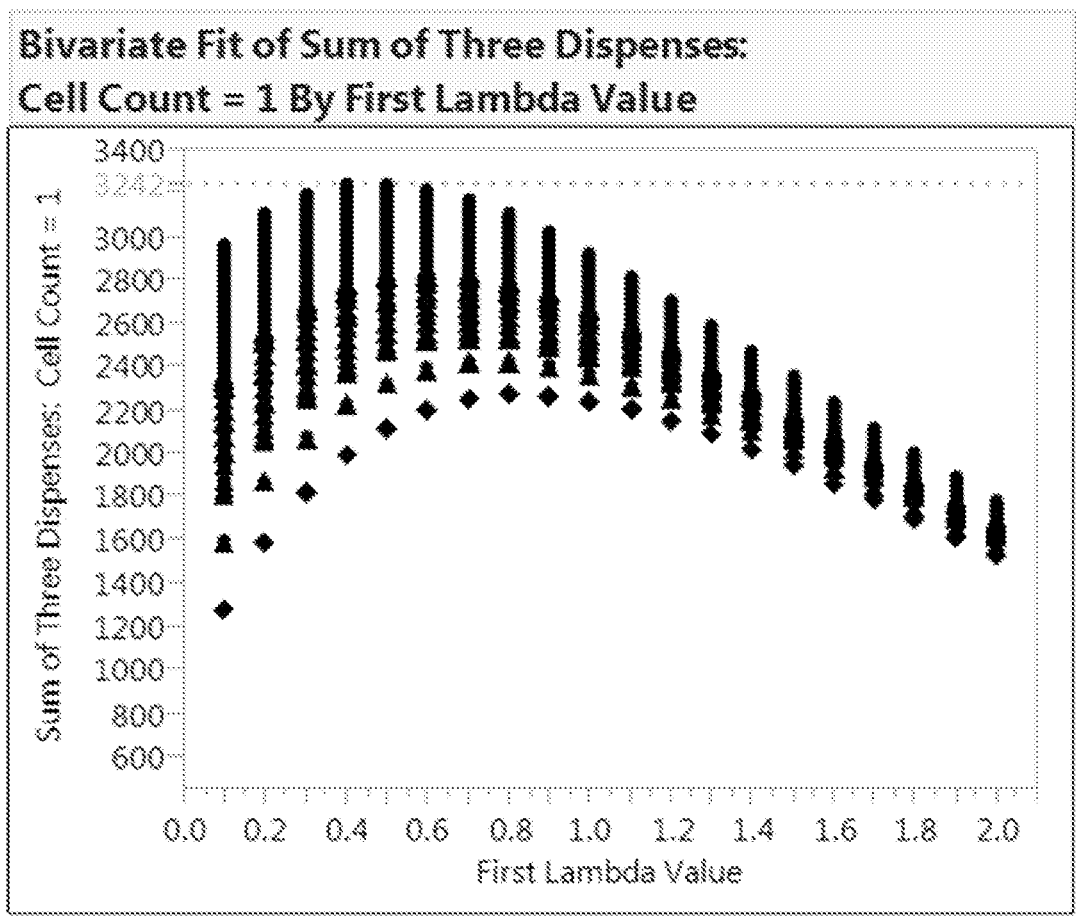
FIG. 7: Theoretical curve fit for an idealized Poisson distribution of cells into the 5,184 well chip format (72×72 format) are shown for the case of using three dispense steps. Here, the number of remaining wells predicted to contain zero cells subsequent to second dispense are identified and subjected to a third MSND Poisson-distributed dispense (RPD). The number of theoretical wells containing a single cell per well after the third dispense are shown as a function of the first lambda (mean) value. The data points for this three-dispense format are shown as black circles in this graph as well as the subsequent graphs in FIGS. 8-9.
Figure 8:
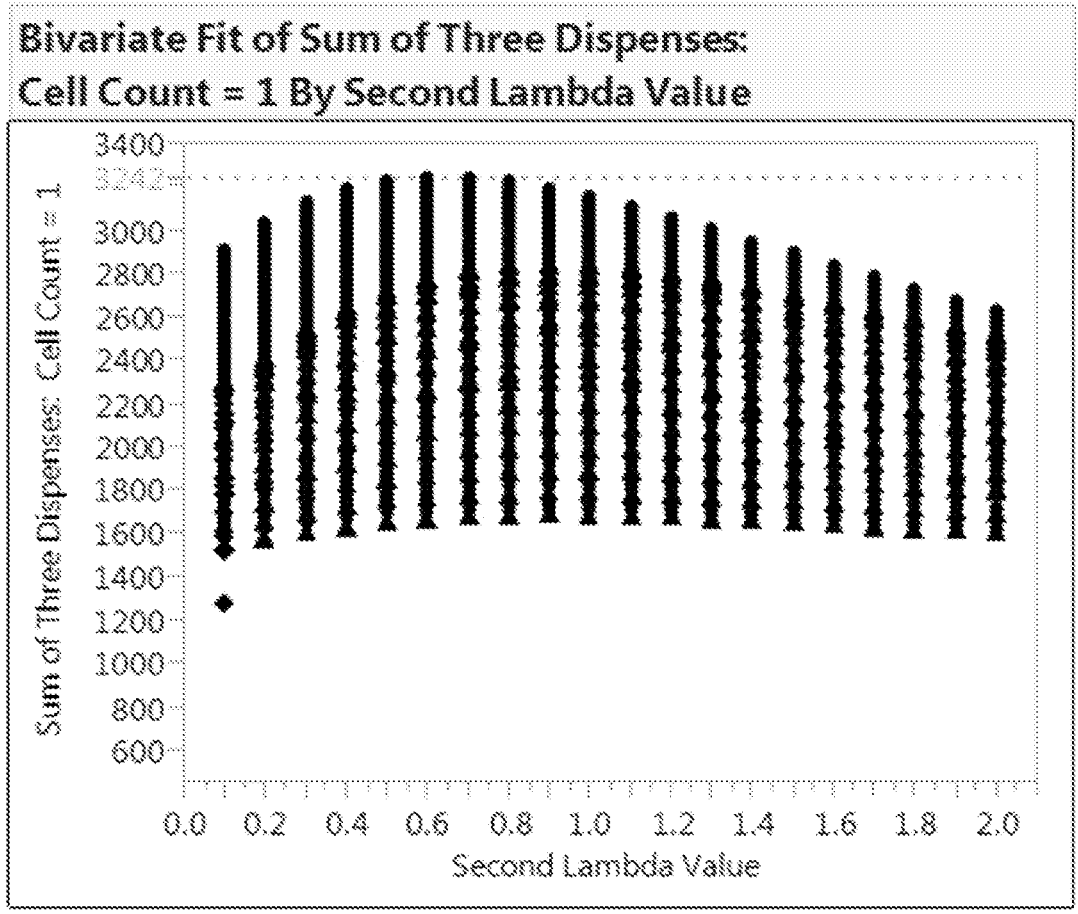
FIG. 8: Theoretical curve fit for an idealized Poisson distribution of cells into the 5,184 well chip format (72×72 format) are shown for the case of using three dispense steps. Here, the number of remaining wells predicted to contain zero cells subsequent to second dispense are identified and subjected to a third MSND Poisson-distributed dispense (RPD). The number of theoretical wells containing a single cell per well after the third dispense are shown as a function of the second lambda (mean) value.
Figure 9:
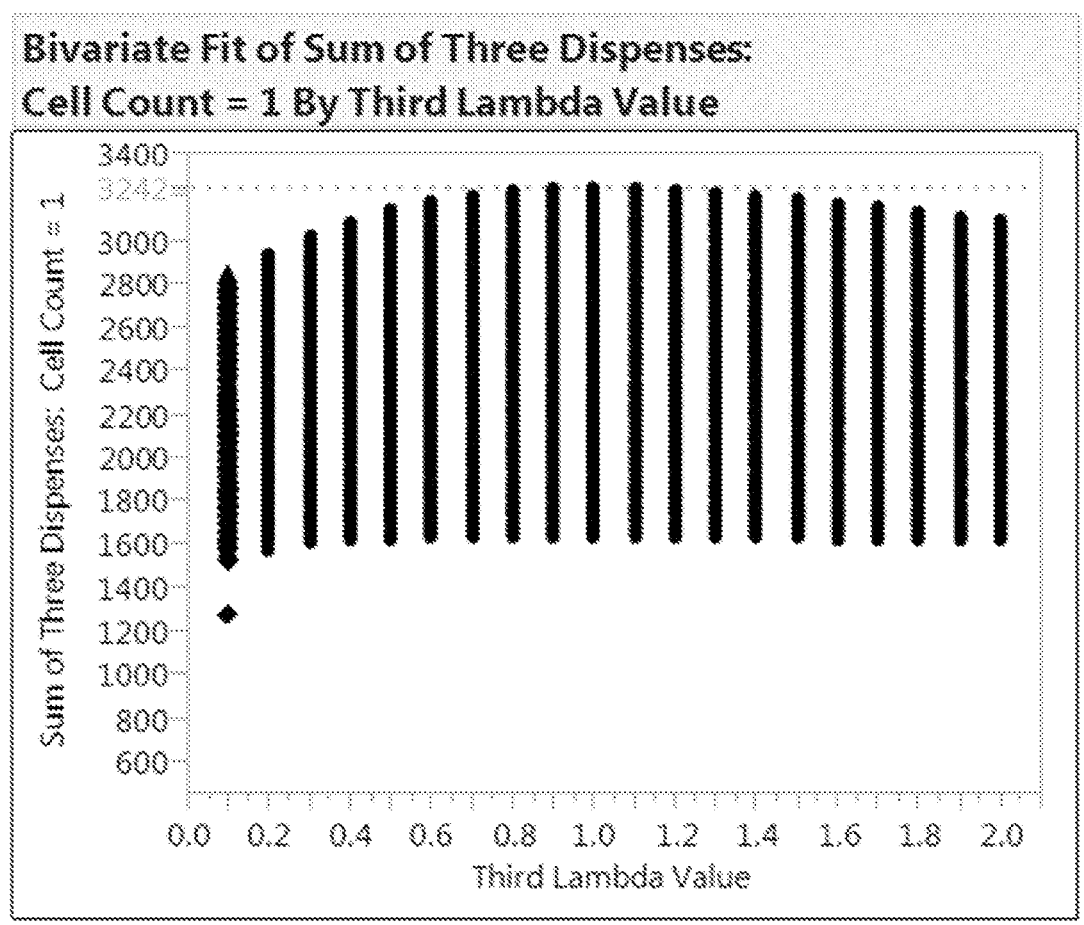
FIG. 9: Theoretical curve fit for an idealized Poisson distribution of cells into the 5,184 well chip format (72×72 format) are shown for the case of using three dispense steps. Here, the number of remaining wells predicted to contain zero cells subsequent to second dispense are identified and subjected to a third MSND Poisson-distributed dispense (RPD). The number of theoretical wells containing a single cell per well after the third dispense are shown as a function of the third lambda (mean) value.
Figure 10:
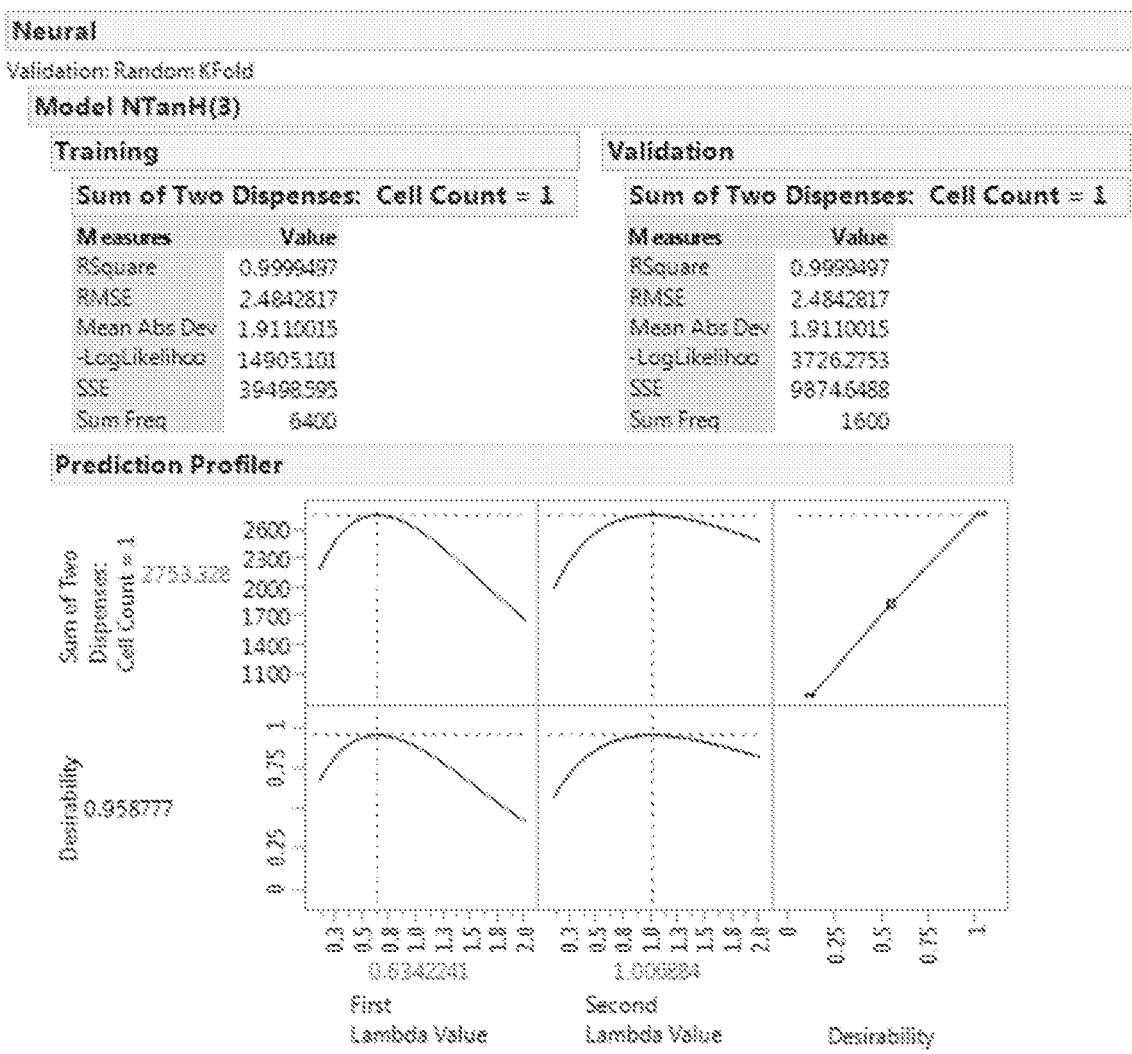
FIG. 10: Data modeling of theoretical iterative Poisson distribution of cells into 5,184 well format (72×72 format). Modelling was performed using Neural Network Model Fitting (JMP version 11 software) using the K-fold validation method with Number of Folds set to 5 and Hidden Nodes set to 3. The response limits for the Sum of the Two Dispenses for Cell Count equal to One (i.e., wells with single-cells) were set to Maximize and the Prediction Profiler was set to Maximize Desirability. Gray typeset in the Prediction Profiler on the two x-axes indicate the optimal predicted lambda for each iteration to achieve the indicated maximal number (shown in gray typeset on the y-axis of single cells) after two total (one engineered) dispense. The optimal predicted lambda values for each of the two dispenses correspond with those in the graphs found in FIGS. 5 and 6.
Figure 11:
FIG. 11: Data modeling of theoretical iterative Poisson distribution of cells into 5,184 well format (72×72 format). Modelling was performed using Neural Network Model Fitting (JMP version 11 software) using the K-fold validation method with Number of Folds set to 10 and Hidden Nodes set to 6. The response limits for the Sum of the Three Dispenses for Cell Count equal to One (i.e., wells with single-cells) were set to Maximize and the Prediction Profiler was set to Maximize Desirability. Gray typeset in the Prediction Profiler on the three x-axes indicate the optimal predicted lambda for each iteration of dispensing to achieve the indicated maximal number (shown in gray typeset on the y-axis of single cells) after three total (two engineered) dispenses. The optimal predicted lambda values for each of the three dispenses correspond with those in the graphs found in FIGS. 7, 8 and 9.

The theoretical basis for increasing the single cell occupancy rate above the statistical limitations of the Poisson distribution for a single dispense step (FIG. 4) were modeled using a statistical software package. An aspect of this disclosure is the ability to utilize the Recursive Poisson Dispense "RPD" to determine which micro-wells contain zero cells and specifically perform a subsequent dispense of cell-containing solution into those wells for a second, third, etc., iteration.

In certain embodiments, automated systems and methods are employed to determine which wells of a multi-well testing device contain the desired number of dispensed cells (e.g., 1 cell per well). In particular embodiments, software for automated imaging and automated well selection is employed to determine which cells contain the desired number of cells. In this regard, a dispense map (e.g., as shown in FIG. 18e) can be generated to show which wells contain the desired number of cell(s) so such cells can be dispensed further reagents and used for further analysis.

One exemplary embodiment, with reference to FIGS. 18 and 19, using a Wafergen 5184 well chip and Hoechst 33342 type and Propidium Iodide florescence is as follows. Once cells have been deposited (e.g., using the Poisson dispensing described herein) into a multi-well test device (e.g., a chip with 5185 wells) via a dispense device (e.g., Wafergen's multi-sample nano-dispenser), image acquisition of every well occurs using a mechanized platform, such as a mechanized microscope stage. Image acquisition is, in some embodiments, collected at 2 wavelengths, commonly consistent with detection of Hoechst 33342 and Propidium Iodide fluorescence. Each image may be composed of a 6×6 array of wells within a 5184 well chip array. Imaging the entire array of 5184 wells generates 144 microscopy image files at each wavelength examined, for a total of 288 images if measured at 2 wavelengths. Well selection software, such as Wafergen's CellSelect™ image analysis software, permits opening the full set of images associated with a given chip array (e.g., SmartChip array). Image analysis consists of 4 main steps: 1) Confirmation of proper orientation of the chip during image acquisition via fiducial well alignment (see FIG. 19), 2) Assessment of location of each well in each of the 288 image files, 3) Identification of potential cells within each well within each image file; and 4) Presentation of the analysis produces a user friendly output annotated by chip well, barcode sequence, examined wavelength and additional parameters of interest.

Figure 19:
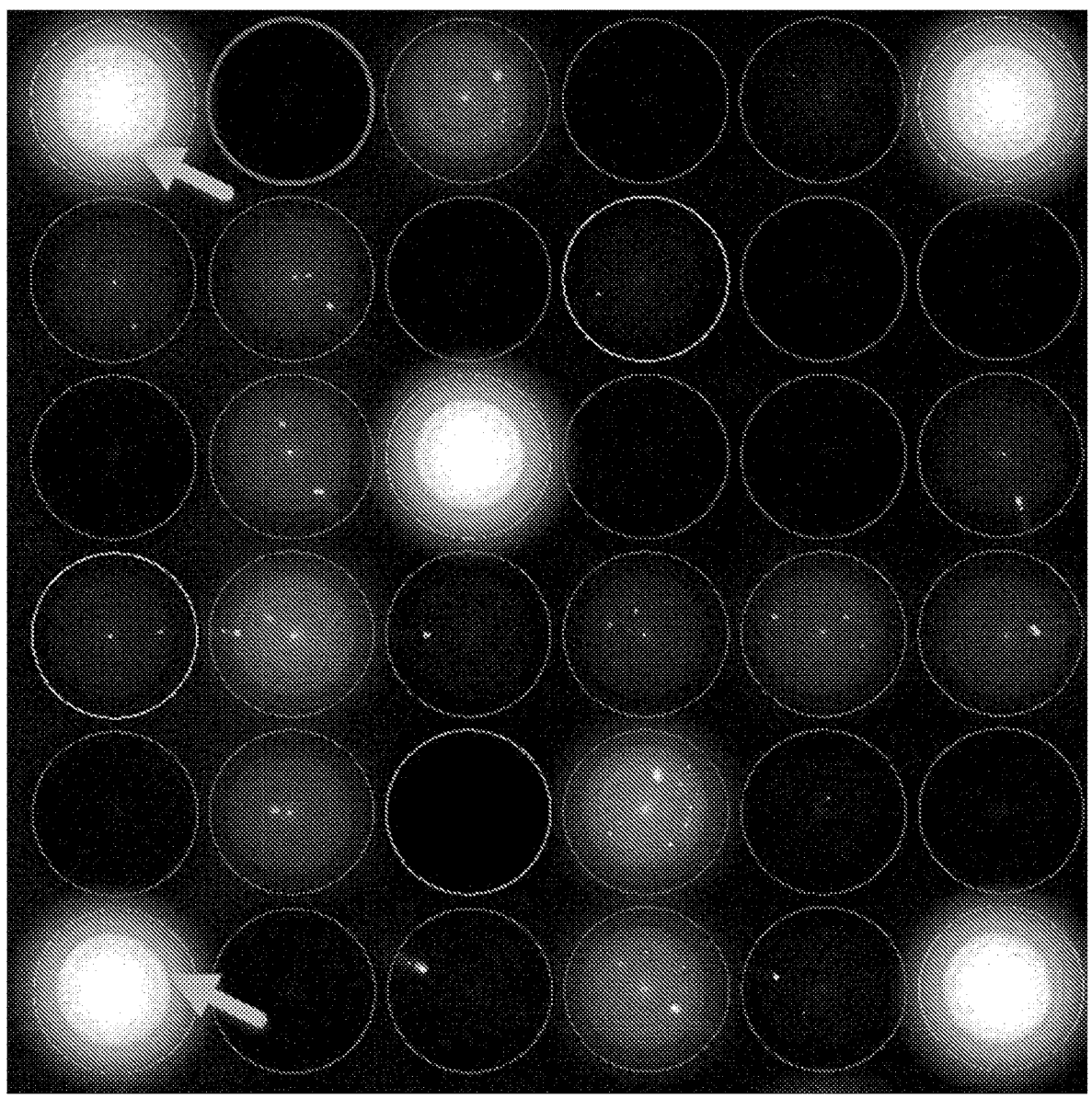
FIG. 19 illustrates an image of a 6×6 array of wells containing fiducial wells. These fiducial wells (5 in this example) contain a fluorescent dye (highlighted by red arrows) which allows the user to ensure the correct orientation of the chip during acquisition and also to infer array well positions.

Confirmation of orientation and assessment of well location is achieved by analysis of a dispensed dye (e.g., fluorescent dye) located in known well positions (fiducial wells) of each chip (see FIG. 19). Fiducial wells may be located at the corners of the chip array in a non-symmetric manner to confirm the correct chip orientation during image acquisition. Similarly, well locations of non-fiducial wells can be inferred based on the known distance between fiducial wells and knowledge of the dimensions of the array structure on the chip array.

Once well locations are identified image analysis is performed to identify the number of objects within each well which meet automated or user defined image analysis thresholds that define the presence or absence of a cell(s). These parameters may include, but are not limited to, object and background fluorescence intensity, size and roundness. In addition, results from multiple wavelengths may be combined for each object to assess parameters such as cell viability. Image analysis results are subsequently summarized by array position (row and column position) and associated with barcodes and image analysis values of any given array position permitting well-level user review.

Importantly, the well selection software (e.g., Wafergen's CellSelect™ image analysis software) will generate a report indicating if a well is a candidate single cell or other user defined well, to receive a dispense of a subsequent reagent. These wells are then used to construct the dispense map or file or filter file used in follow-on biochemistry steps.

Figure 18A:
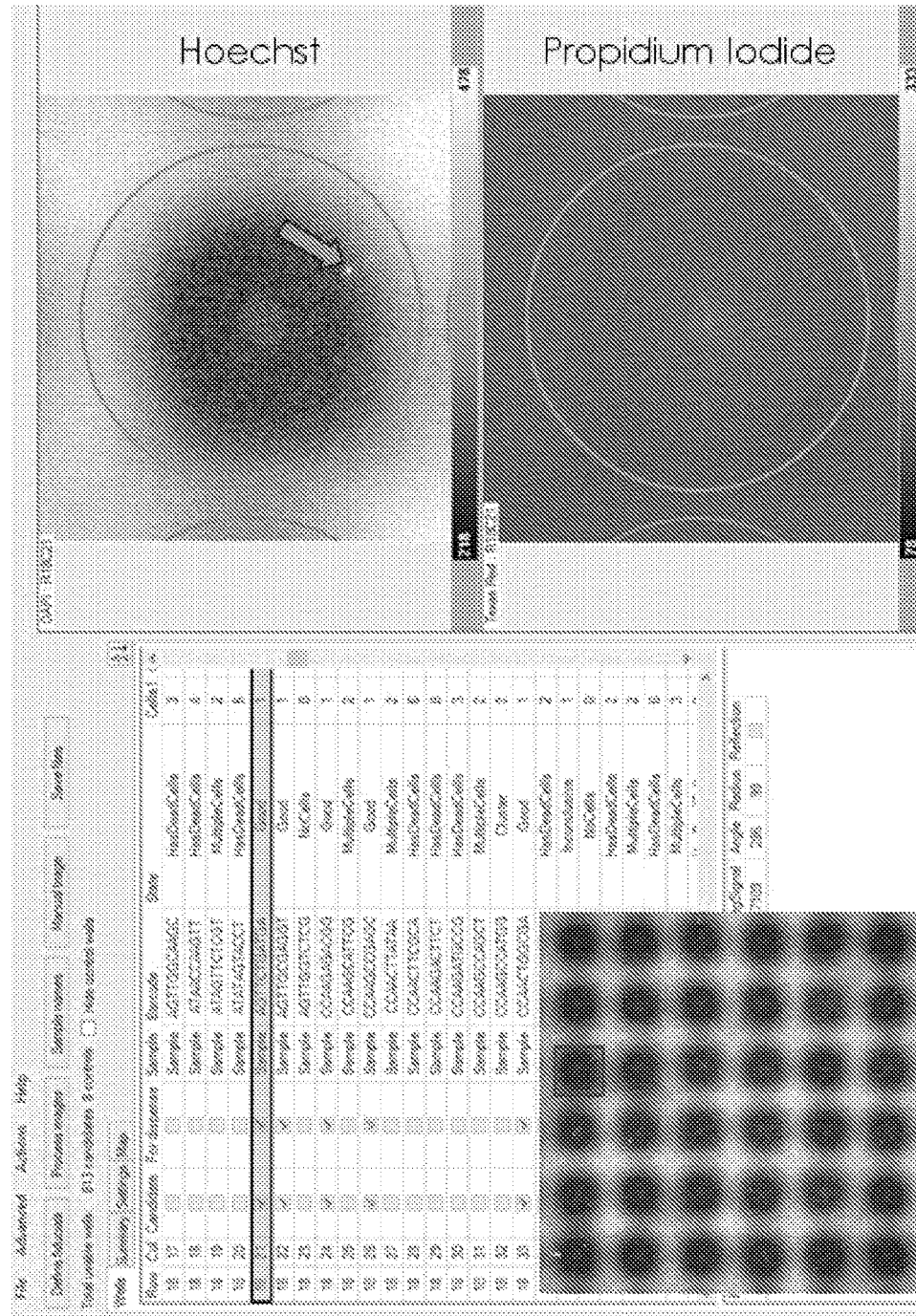
Figure 18C:
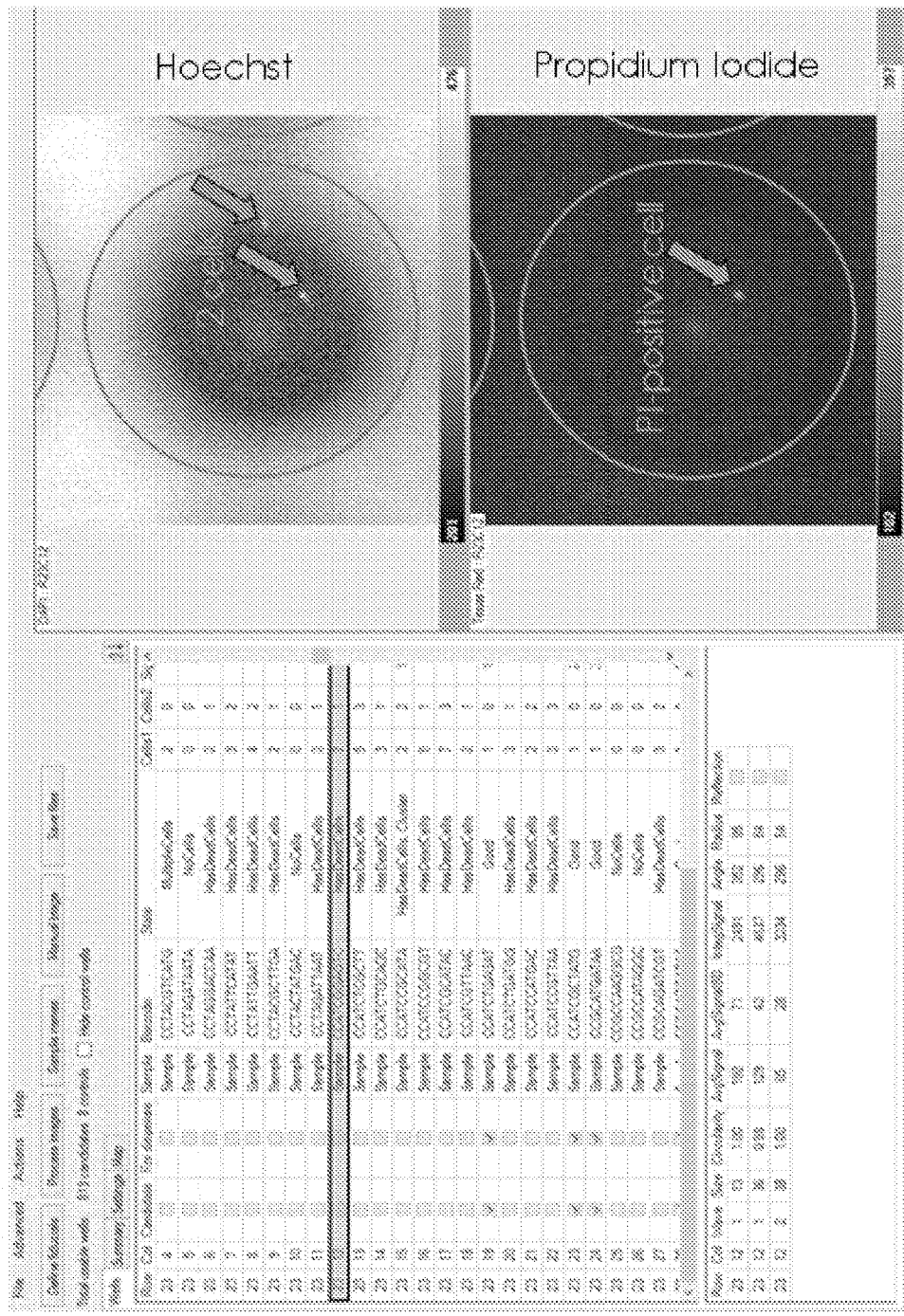
Figure 18D:
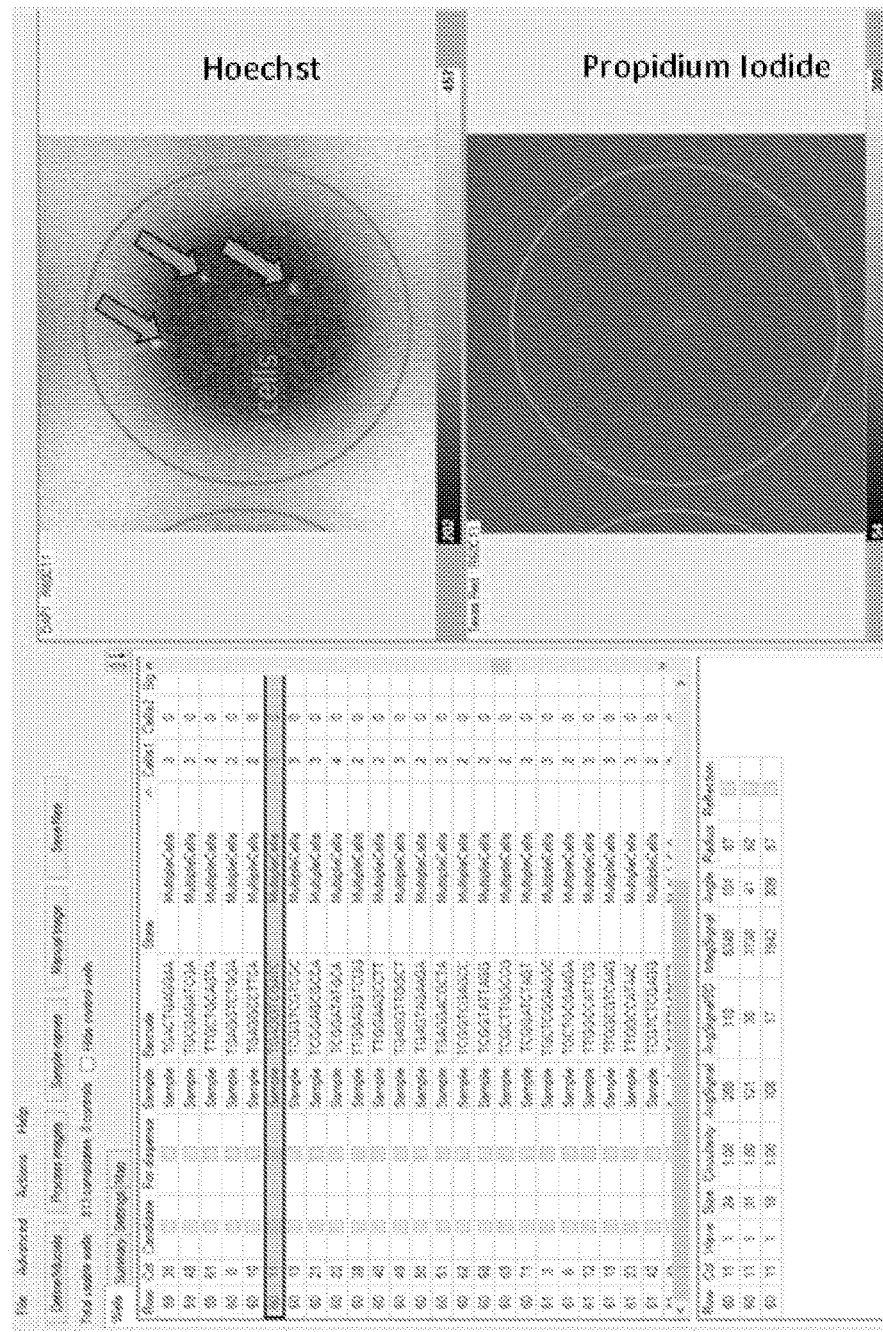
Figure 18E:
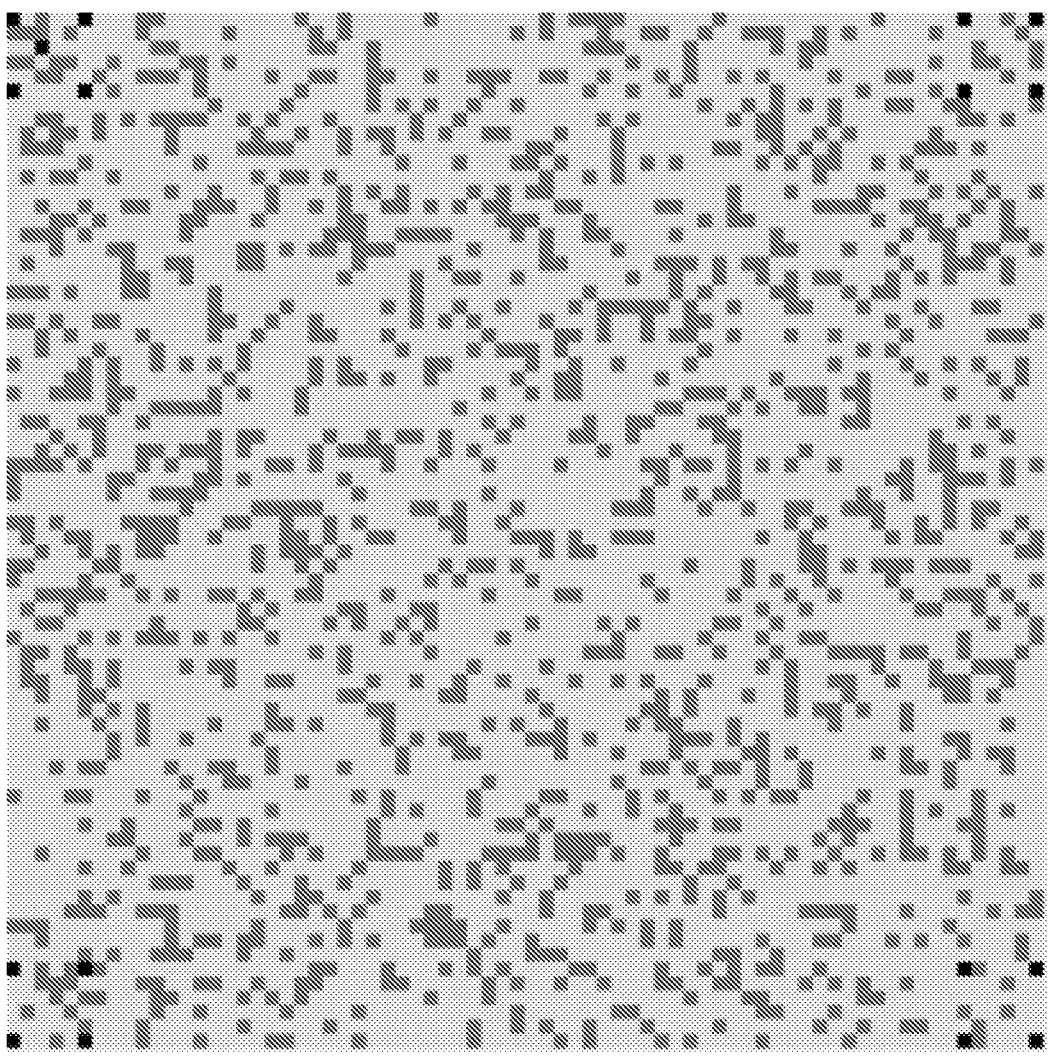

Example output from CellSelect™ image analysis software is presented in FIGS. 18a-18d. In FIG. 18a, a well is presented in row/column position 18/21. Results from this well and its associated images are presented and identify this well as a candidate for inclusion in a dispense file or dispense map. This well contains a single viable cell (indicated by the arrow) illustrating the presence of an object meeting appropriate image analysis thresholds and/or user preferences. In the Hoechst fluorescence image of a single well, (top right panel) there is no obvious corresponding signal in the propidium iodide channel (bottom right panel). FIG. 18b illustrates an example of a well not selected as candidates for inclusion in a dispense map due to analysis resulting in an object being flagged as a potential cell multiplet, cell cluster. FIG. 18c indicates exclusion of well containing greater than 1 cell or exclusion by signal detection in the propodium iodide channel. FIG. 18d illustrates an example of a well that is excluded by the software because it contains three cells.

Upon completion of analysis of all imaged wells, a reagent dispense map (aka a "dispense or filter file") or is created. Well selection and subsequent dispense file mapping can be completely automated or user-edited in CellSelect software (or other well selection software) to either include or exclude wells per user requirements. This dispense map is used to program a dispensing component, such as Wafergen's MSND, to selectively deliver reagents to appropriate wells for further processing such as reverse transcription. FIG. 18e illustrates a typical CellSelect™ image analysis software generated sample dispense map that localizes single cells deposited in a standard WaferGen 72×72 chip array. Typically, each dispense and analysis event generates a unique dispense map which is annotated with unique chip ID. FIG. 18e provides a schematic of a dispense map highlighting specific wells chosen for reagent dispense for further upstream processing.

The present disclosure is not limited by the type of cells that are employed. In certain embodiments, cancer cells, circulating cancer cells, stem cells, and cancer stem cells are employed. Most cancer deaths appear to be caused by metastatic spread and growth by circulating tumor cells at distant organs. Circulating tumor cells (CTCs), CTC clusters (two or more individual CTCs bound together), and cancer stem cells (CSCs) may be initially localized, latent systemic, or post-adjuvant treatment depleted. Consequently, CTCs and the relevant stem cells are frequently present at low numbers within a large background of normal non-cancerous cells. The low frequency of these cells generates a complex "needle in a haystack" analysis problem for detecting the required cancer cell signal within the large 'noise' background. Detection of cancer cell specific cell surface markers and analysis of these cells is deeply relevant to understanding the biology of metastatic spread. The methods and systems provided herein allow isolation and analysis of such important cancer cells.

Single-cell, multiple-cell and cell clusters may initially be either enriched or depleted from a cell or tissue milieu or population, based on the presence of antigenic/phenotypic cell-surface or intra-cellular markers including but not restricted to: protein, lipid, carbohydrate (i.e. glycosylation) post-translational modifications of those moieties, nucleic acids and their modifications, or varying combinations of these moieties. Detection of cell surface markers in single cells—including cancer cells—and transferring those cells into discrete individual wells of a microfluidic device (e.g., Wafergen's SmartChip wells) is performed with the methods and systems described herein. In other embodiments, labelled cells may be dispensed directly into wells and antigenic moieties detected directly in chip via standard or automated microscopy using a variety of widely available fluorescence filters.

Methods of circulating tumor cell (CTC) enrichment and visualization are known in the art and may be employed for generating (and later visualizing) the initial cell suspension employed in the methods and systems described herein. For example, Table 1 of Krebs et al. Nat Rev Clin Oncol. 2014 March; 11(3):129-44 (herein incorporated by reference, and specifically with respect to Table 1). Examples of markers that can be employed to enrich and visualize CTCs include, but are not limited to: CD45, EpCAM, MUC1, and HER2. Antibodies to such markers may be employed to label and visualize such cells. Any type of suitable method may be employed for isolating and enriching CTCs, such as flow cytometry, column binding, etc.

The present disclosure is not limited by the type of multi-well testing devices (e.g., plates or chips) employed. In general, such devices have a plurality of wells that contain, or are dimensioned to contain, liquid (e.g., liquid that is trapped in the wells such that gravity alone cannot make the liquid flow out of the wells). One exemplary chip is WAFERGEN's 5184-well SMARTCHIP. Other exemplary chips are provided in U.S. Pat. Nos. 8,252,581; 7,833, 709; and 7,547,556, all of which are herein incorporated by reference in their entireties including, for example, for the teaching of chips, wells, thermocycling conditions, and associated reagents used therein). Other exemplary chips include the OPENARRAY plates used in the QUANTSTUDIO real-time PCR system (Applied Biosystems). Another exemplary multi-well device is a 96-well or 384-well plate.

The overall size of the multi-well devices may vary and it can range, for example, from a few microns to a few centimeters in thickness, and from a few millimeters to 50 centimeters in width or length. Typically, the size of the entire device ranges from about 10 mm to about 200 mm in width and/or length, and about 1 mm to about 10 mm in thickness. In some embodiments, the chip is about 40 mm in width by 40 mm in length by 3 mm in thickness.

The total number of wells (e.g., nanowells) on the multi-well device may vary depending on the particular application in which the subject chips are to be employed. The density of the wells on the chip surface may vary depending on the particular application. The density of wells, and the size and volume of wells, may vary depending on the desired application and such factors as, for example, the species of the organism for which the methods of this disclosure are to be employed.

The present disclosure is not limited by the number of wells in the multi-well device or the number of wells in the multi-well source device. A large number of wells may be incorporated into a device. In various embodiments, the total number of wells on the device is from about 100 to about 200,000, or from about 5000 to about 10,000. In other embodiments the device comprises smaller chips, each of which comprises about 5,000 to about 20,000 wells. For example, a square chip may comprise 125 by 125 nanowells, with a diameter of 0.1 mm.

The wells (e.g., nanowells) in the multi-well devices may be fabricated in any convenient size, shape or volume. The well may be about 100 µm to about 1 mm in length, about 100 µm to about 1 mm in width, and about 100 µm to about 1 mm in depth. In various embodiments, each nanowell has an aspect ratio (ratio of depth to width) of from about 1 to about 4. In one embodiment, each nanowell has an aspect ratio of about 2. The transverse sectional area may be circular, elliptical, oval, conical, rectangular, triangular, polyhedral, or in any other shape. The transverse area at any given depth of the well may also vary in size and shape.

In certain embodiments, the wells have a volume of from about 0.1 nl to about 1 ul. The nanowell typically has a volume of less than 1 ul, preferably less than 500 nl. The volume may be less than 200 nl, or less than 100 nl. In an embodiment, the volume of the nanowell is about 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

A well of high inner surface to volume ratio may be coated with materials to reduce the possibility that the reactants contained therein may interact with the inner surfaces of the well if this is desired. Coating is particularly useful if the reagents are prone to interact or adhere to the inner surfaces undesirably. Depending on the properties of the reactants, hydrophobic or hydrophilic coatings may be selected. A variety of appropriate coating materials are available in the art. Some of the materials may covalently adhere to the surface, others may attach to the surface via non-covalent interactions. Non-limiting examples of coating materials include silanization reagent such as dimethylchlorosilane, dimethyldichlorosilane, hexamethyldisilazane or trimethylchlorosilane, polymaleimide, and siliconizing reagents such as silicon oxide, AQUASIL, and SURFASIL. Additional suitable coating materials are blocking agents such as amino acids, or polymers including but not limited to polyvinylpyrrolidone, polyadenylic acid and polymaleimide. Certain coating materials can be cross-linked to the surface via heating, radiation, and by chemical reactions. Those skilled in the art will know of other suitable means for coating a nanowell of a multi-well device, or will be able to ascertain such, without undue experimentation.

An exemplary multi-well device (e.g., chip) may have a thickness of about 0.625 mm, with a well have having dimensions of about 0.25 mm (250 um) in length and width. The nanowell depth can be about 0.525 mm (525 um), leaving about 0.1 mm of the chip beneath a given well. A nanowell opening can include any shape, such as round, square, rectangle or any other desired geometric shape. By way of example, a nanowell can include a diameter or width of between about 100 µm and about 1 mm, a pitch or length of between about 150 µm and about 1 mm and a depth of between about 10 µm to about 1 mm. The cavity of each well may take a variety of configurations. For instance, the cavity within a nanowell may be divided by linear or curved walls to form separate but adjacent compartments.

The wells (e.g., nanowells) of the multi-well device may be formed using, for example, commonly known photolithography techniques. The nanowells may be formed using a wet KOH etching technique, an anisotropic dry etching technique, mechanical drilling, injection molding and or thermo forming (e.g., hot embossing).

Reagents contained within the liquid in the multi-well device depend on the reaction that is to be run with the single cell that is deposited into each well. In an embodiment, the wells contain a reagent for conducting the nucleic acid amplification reaction. Reagents can be reagents for immunoassays, nucleic acid detection assays including but not limited to nucleic acid amplification. Reagents can be in a dry state or a liquid state in a unit of the chip. In an embodiment, the wells contain at least one of the following reagents: a probe, a polymerase, and dNTPs. In another embodiment, the wells contain a solution comprising a probe, a primer and a polymerase. In various embodiments, each well comprises (1) a primer for a polynucleotide target within said standard genome, and (2) a probe associated with said primer which emits a concentration dependent signal if the primer binds with said target. In various embodiments, each well comprises a primer for a polynucleotide target within a genome, and a probe associated with the primer which emits a concentration dependent signal if the primer binds with the target. In another embodiment, at least one well of the chip contains a solution that comprises a forward PCR primer, a reverse PCR primer, and at least one FAM labeled MGB quenched PCR probe. In an embodiment, primer pairs are dispensed into a well and then dried, such as by freezing. The user can then selectively dispense, such as nano-dispense, the sample, probe and/or polymerase.

In other embodiments of the disclosure, the wells may contain any of the above solutions in a dried form. In this embodiment, this dried form may be coated to the wells or be directed to the bottom of the well. The user can add a mixture of water and the captured cells to each of the wells before analysis. In this embodiment, the chip comprising the dried down reaction mixture may be sealed with a liner, stored or shipped to another location.

The multi-well devices, with a single cell in each well, may be used for genotyping, gene expression, or other DNA assays preformed by PCR. Assays performed in the plate are not limited to DNA assays such as TAQMAN, TAQMAN Gold, SYBR gold, and SYBR green but also include other assays such as receptor binding, enzyme, and other high throughput screening assays.

In some embodiments cells are subjected (e.g., after lysis and/or other processing steps) to amplification and/or sequencing analysis. Conducting one or more amplification reactions may comprise one or more PCR-based amplifications, non-PCR based amplifications, or a combination thereof. Illustrative non-limiting examples of nucleic acid amplification techniques include, but are not limited to, polymerase chain reaction (PCR), reverse transcription polymerase chain reaction (RT-PCR), nested PCR, linear amplification, multiple displacement amplification (MDA), real-time SDA, rolling circle amplification, circle-to-circle amplification transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to permit exponential increase in copy numbers of target nucleic acids. In a variation called RT-PCR, reverse transcriptase (RT) is used to make a complementary DNA (cDNA) from RNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat.

Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemi-phosphorothioated primer extension product, endonuclease-mediated nicking of a hemi-modified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

In some embodiments, nucleic acid sequencing methods are utilized (e.g., for detection of amplified nucleic acids). In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306, 597 to Macevicz et al., both of which are herein incorporated by reference in their entireties). Additional examples of sequencing techniques in which the technology finds use include the Church polony technology (Mitra et al., 2003, *Analytical Biochemistry* 320, 55-65; Shendure et al., 2005 *Science* 309, 1728-1732; U.S. Pat. Nos. 6,432,360, 6,485, 944, 6,511,803; herein incorporated by reference in their entireties), the 454 picotiter pyrosequencing technology (Margulies et al., 2005 *Nature* 437, 376-380; US 20050130173; herein incorporated by reference in their entireties), the Solexa single base addition technology (Bennett et al., 2005, *Pharmacogenomics*, 6, 373-382; U.S. Pat. Nos. 6,787,308; 6,833,246; herein incorporated by reference in their entireties), the Lynx massively parallel signature sequencing technology (Brenner et al. (2000). *Nat. Biotechnol.* 18:630-634; U.S. Pat. Nos. 5,695,934; 5,714,330; herein incorporated by reference in their entireties), and the Adessi PCR colony technology (Adessi et al. (2000). *Nucleic Acid Res.* 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.,* 55: 641-658, 2009; MacLean et al., *Nature Rev. Microbiol.,* 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.,* 55: 641-658, 2009; MacLean et al., *Nature Rev. Microbiol.,* 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.,* 55: 641-658, 2009; MacLean et al., *Nature Rev. Microbiol.,* 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specific color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics is used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Reagents for any suitable type of assay may be added to the wells of the multi-well chip (e.g., using a multi-well dispenser, such as the one from WAFERGEN BIOSYSTEMS). Such reagents may be added to the wells before or after a cell (e.g., a single cell) is added to a well. In certain embodiments, protein detection assay components (e.g., anti-body based assays) are added to the wells. In other embodiments, SNP detection assay components are added to the wells. In other embodiments, nucleic acid sequencing assay components are added to the wells. In certain embodiments, nucleic acid sequence assay components that employ barcoding for labelling individual mRNA molecules, and/or for labeling for cell/well source (e.g., if wells pooled before sequencing analysis), and/or for labeling particular multi-well chips (e.g., if wells from two or more multi-well chips are pooled prior to sequencing) are employed. Examples of such barcoding methodologies and reagents are found in Pat. Pub. US2007/0020640, Pat. Pub. 2012/0010091, U.S. Pat. Nos. 8,835,358, 8,481,292, Qiu et al. (Plant. Physiol., 133, 475-481, 2003), Parameswaran et al. (Nucleic Acids Res. 2007 October; 35(19): e130), Craig et al. reference (Nat. Methods, 2008, October, 5(10):887-893), Bontoux et al. (Lab Chip, 2008, 8:443-450), Esumi et al. (Neuro. Res., 2008, 60:439-451), Hug et al., J. Theor., Biol., 2003, 221: 615-624), Sutcliffe et al. (PNAS, 97(5):1976-1981; 2000), Hollas and Schuler (Lecture Notes in Computer Science Volume 2812, 2003, pp 55-62), and WO201420127; all of which are herein incorporated by reference in their entireties, including for reaction conditions and reagents related to barcoding and sequencing of nucleic acids.

In certain embodiments, the barcode tagging and sequencing methods of WO2014201272 ("SCRB-seq" method) are employed. The necessary reagents for the SCRB-seq method (e.g., modified as necessary for small volumes) are added to the wells of the multi-well chips (e.g., where the single cell in the well has been lysed). Briefly, the SCRB-seq method amplifies an initial mRNA sample from a single cell in multi-well plates (as described above), where each well has a single cell. Initial cDNA synthesis uses a first primer with: i) N6 or N11 for cell/well identification, ii) N10 for particular molecule identification, iii) a poly T stretch to bind mRNA, and iv) a region that creates a region where a second template-switching primer will hybridize. The second primer is a template switching primer with a poly G 3' end, and 5' end that has iso-bases. After cDNA amplification, the tagged cDNA single cell/well samples are pooled. Then full-length cDNA synthesis occurs with two different primers, and full-length cDNA is purified. Next, a NEXTERA sequencing library is prepared using an i7 primer (adds one of 12 i7 tags to identify particular multi-well plates) and PSNEXTPTS to add P5 tag for NEXTERA sequencing (P7 tag added to other end for NEXTERA). The library is purified on a gel, and then NEXTERA sequencing occurs. As a non-liming example, with twelve i7 plate tags, and 384 cell/well-specific barcodes, this allows total of 4,608 single cell transcriptomes to be done at once. This method allows for quantification of mRNA transcripts in single cells and allows users to count the absolute number of transcript molecules/cell to remove any variables from normalization.

In further embodiments image and chip mapped wells within the chip are dynamically and/or statically selected for further analysis by a combination of single or multiple addition of reagents for detection and/or resolution of nucleic acids or lipids or carbohydrates or protein cell components reagents.

EXAMPLES

Example 1

Isolating Single Cancer Cells in a Multi-Well Chip

Figure 12:
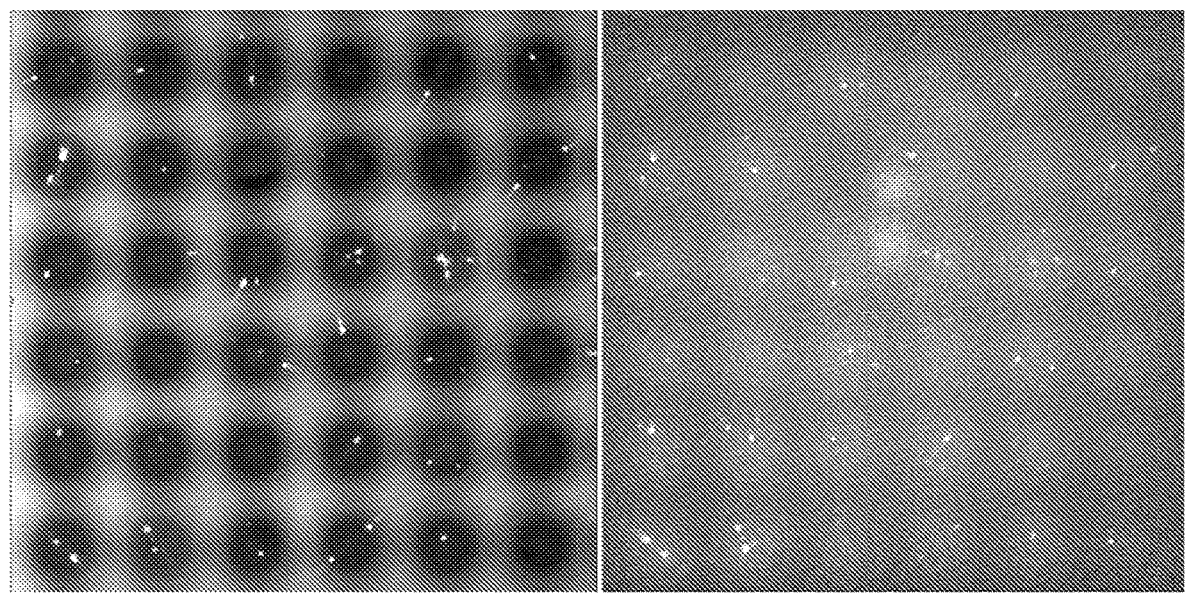
FIG. 12: A 4× objective microscope field of view displaying 36 of 5184 wells visualized in a 150 nL chip. SK-BR-3 cells were dual-stained with Hoechst 33342 dye and the APC-conjugated monoclonal antibody targeting the HER2/neu antigen. All SK-BR-3 cells stain with Hoechst 33342 supravital dye (left panel). The adjacent right panel indicates the same 36-well FOV in which the SK-BR-3 (HER2/neu/ERBB2-positive) cells were treated with an antibody specific for this cell surface antigen. A comparison of the two images in FIG. 12 indicates the Hoechst signal specifically overlaps with the conjugated antibody-generated signal obtained from the Cy5 filter set.
Figure 13:
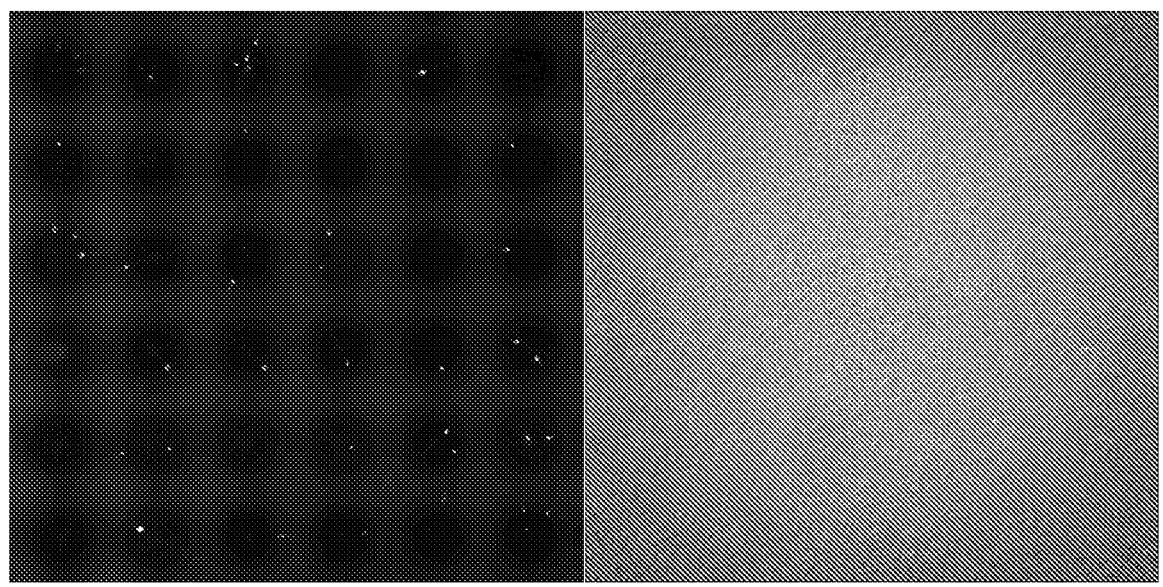
FIG. 13: A 4× objective microscope field of view displaying 36 of 5184 wells visualized in a 150 nL chip. SK-BR-3 cells were dual-stained with Hoechst 33342 dye and the negative control Ab targeting mouse IgG2B-APC. All SK-BR-3 cells stain with Hoechst 33342 supravital dye (left panel). The adjacent right panel indicates the same 36-well FOV in which the SK-BR-3 (HER2/neu/ERBB2-positive) cells were treated with an antibody that was not specific for this cell surface antigen. A comparison of the two images in FIG. 13 indicates the Hoechst signal does not overlap with the negative control antibody-generated signal obtained from the Cy5 filter set.

An example of the use of cell surface markers including positive and negative control antibody (Ab) staining, dispense and imaging of single and multiple cells in a Wafergen chip is shown in FIGS. 12 and 13 respectively. FIGS. 12 and 13 illustrate a 36 well field of view (FOV) well-level image following trypsinisation-release from tissue culture flasks, resuspension, staining and imaging starting with ~30,000 human breast cancer SK-BR-3 cells, a immortalized cultured cell line known to be strongly HER2/neu/ERBB2-positive from the literature.

SK-BR-3 cells were washed and collected into 1 mL of 1×PBS (no Mg++, no Ca++, pH 7.4; 37° C.). One-half of the volume of the above suspension was incubated with 10 uL of an appropriate, conjugated monoclonal antibody (mouse anti-human ERBB2 (HER2)-APC; R&D Systems; FAB1129A) against the cell surface antigen ERBB2 (HER2/neu). The remaining half-volume of the suspension was incubated in parallel with an appropriate negative control antibody for immunostaining, namely, a conjugated, isotype-matched control antibody (mouse IgG2B-APC; R&D Systems; IC0041A).

In brief, conjugated antibody incubations were performed at 37° C. for one hour. Subsequently, a volume of 4.5 mL of pre-warmed 1×PBS (37° C.) was added, and the cells were centrifuged at 200×g for 5 minutes at room temperature. Pelleted cells were resuspended in 200 μL of pre-warmed 1×PBS (37° C.) then stained for ~20 minutes in 1× Hoechst 33342 supravital stain at 37° C. Eighty microliter aliquots of each suspension were dispensed into the appropriate receiving wells of a 384-well plate. A Wafergen MSND (multi-sample nanodispenser; see U.S. application Ser. No. 14/738, 183, herein incorporated by reference in its entirety) was used to aspirate cells from the 384-well receiving plate (see, e.g., FIGS. 1-3). Each 50 nL dispense volume was calculated to deliver, on average, approximately one antibody- and Hoechst-stained cell per individual wells of the 72×72 well Wafergen SmartChip. Post-dispense, the chip was sealed with Wafergen chip cover film and centrifuged at 300×g at 37° C. to collect cells at the bottom of the Wafergen Smartchip wells. Standard microscopy image collection using an automated microscope stage and a 4× objective was performed. A total of 144 Hoechst 33342 and the corresponding 144 APC-Cy5 images were acquired (~200 or 500 mS exposure for Hoescht and Cy5 respectively) and saved as TIFF files from the 5184-well chip. Each of the 144 images represents 36 individual wells within the 5184 well Wafergen SmartChip array. The chip dispense and image collection process is shown in FIG. 1.

A field of view (FOV), displaying 36 individual wells on a chip, indicates a batch of SK-BR-3 cells that were dual-stained with Hoechst 33342 dye and the APC-conjugated monoclonal antibody targeting the HER2/neu antigen. All of the SK-BR-3 cells are expected to stain using Hoechst 33342 supravital dye (FIG. 12, left panel). The adjacent image indicates the same 36-well FOV in which the SK-BR-3 (HER2/neu/ERBB2-positive) cells were treated with the antibody that is specific for this cell surface antigen (FIG. 12, right panel). Single cells are readily identified as bright dots within the chip wells. A comparison of the two images in FIG. 12 indicates the Hoechst signal (obtained using the DAPI filter set) specifically overlaps with the conjugated antibody-generated signal (obtained from the Cy5 filter set).

A second field of view displaying 36 individual wells from a different region of the same 5184 well chip shows a batch of SK-BR-3 cells that were dual-stained with Hoechst 33342 dye and the APC-conjugated negative control monoclonal antibody mouse IgG2B-APC (FIG. 13). A comparison of Hoechst stained cells (FIG. 13, left panel) with the negative control antibody-stained cells (FIG. 13, right panel) does not indicate an overlap of the Hoechst signal with the negative control antibody-generated signal.

The image data in FIG. 12 indicates the use of a positive control antibody provides cell antigen specific antibody staining of single and multiple cells in a multi-well chip (e.g., Wafergen multi-well chip). In FIG. 13, taken from the same chip, a non-specific antibody does not generate a discrete punctate signal that overlaps with the Hoechst staining signal. Taken together, this Example, with results in FIGS. 12 and 13, demonstrate an exemplary system and process that can be used to dispense and subsequently detect cell surface epitope-specific immunostaining in either single or multiple cancer cells.

Example 2

Isolation of Single Cells from Mixtures of Different Cells

In this example, three samples were examined. Two samples were composed of a single species: human U87-MG-(Red Fluorescent protein positive) cells or mouse NIH/3T3 cells. The third sample was composed of a mixture of the individual single species samples. Cells were stained and dispensed using an MSND (multi-sample nano-dispenser; Wafergen Inc.) permitting a Poisson distribution of cell counts in the wells of a WaferGen SMARTCHIP array. That array was subsequently imaged, and single-cell containing wells selected and other analyte containing wells were selected to be processed into first and second strand cDNA. The cDNA was extracted from the chip using the methods described earlier. The cDNA was PCR amplified off-chip to yield DNA amplicon "libraries" suitable for NGS amplification and readout. Sequence reads from the sample libraries can then be mapped to the specific sample (i.e species genome) to confirm firstly that the cell and RT buffer selection process were capable of selecting specific wells, and secondly, that selected wells from the mixed cell sample give rise to sequencing reads mapping to only one species. In effect, the latter can be used to calculate the single cell occupancy and partitioning ability of the system.

In brief, human U87-MG-RFP and mouse NIH 3T3 cells were separately washed in 1×PBS, counted and stained with Hoechst 33342 and propidium iodide. For cell mixtures, an aliquot of each cell line was mixed in 1:1 ratio. RNA derived from K562 cells (12 pg) and 1×PBS were employed as positive and negative process controls respectively.

Samples and controls were loaded in a 384-well source plate for dispense onto a SmartChip array using the Multi-sample Nanodispenser (MSND). Each well of the Smart-Chip array contains a pre-printed sample identifying "barcode" primer where the 3' oligodT sequence on those primers is used to anneal to polyadenylated stretches of nucleic acid sequences. The barcodes serve as molecular addresses for the mRNA molecules captured from each cell after lysis. Post control and sample dispense, the array was blotted, sealed and centrifuged at 300×g for 5 minutes at 22° C. The array was then imaged. Post-imaging, the array was placed in a freezer (−80° C.) to await cell and sample selection and subsequent reagent addition. Single cells and other analyte containing wells were selected based on their Hoechst 33342 signal using CellSelect™ image analysis software.

A total of 1,268 "single-cell" containing wells were identified. Of these 1,268 wells, 90 wells of each single species cells, 382 wells from the mixed cell sample alongside 4 each of the positive and negative control wells, were also selected for processing. Once well selection was complete, those wells were mapped to receive RT reagents. In brief, the array was removed from the freezer, thawed at room temperature for 10 minutes and centrifuged at 3,220×g for 3 minutes at 4° C. The array was placed in a thermal cycler and barcoded oligodT primers in each well were permitted to anneal to polyadenylated stretches in nucleic acids (primarily mRNA) after nucleic acid temperature denaturation (3 minutes at 72° C.) and annealing during a combined centrifugation/temperature step (3,220×g for 3 minutes at 4° C.). The array was transferred to the MSND for RT dispense. Using the dispense map created by the analysis software, 50 nL of an RT mix containing MMLV RT and a second strand synthesis "template switching oligo" were added to selected wells. The array was centrifuged at 3,220×g for 3 minutes at 4° C. to localize the array contents in each well and incubated for 90 minutes at 42° C. Pooled (barcoded) sample cDNA products were collected via second centrifugation (as above) after inverting the chip and placing into an extraction device (as described in U.S. Pat. Pub. 2014/0130885, Ser. No. 14/075,631, which is herein incorporated by reference in its entirety). Post extraction single primer PCR was performed off chip. Amplicons were fragmented using a transposase based method. Amplicons were enriched for sequences representing 3' ends of mRNAs, (Soumillion et. al., http:// followed by dx.doi.org/10.1101/003236_2014; see also WO 2014/201273; both of which are herein incorporated by reference) and sequenced using a HiSeq 2500 in rapid run mode.

Figure 17:
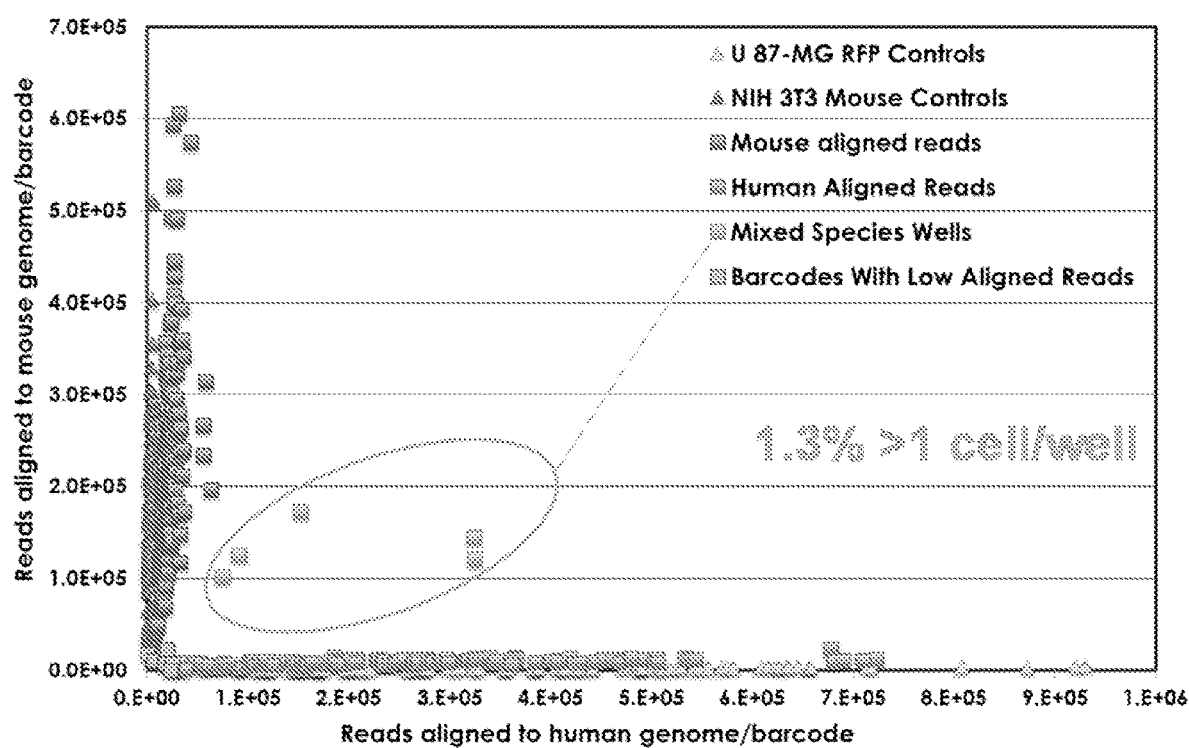
FIG. 17: shows a plot of aligned genomic reads to non-homologous genomic regions for single species samples (U 87-MG-RFP and NIH 3T3) and also mixed species samples as described in Example 2. Data points clustered off-axis represent well populations with more than one cell type per well.

After sequencing, reads from single-species samples and the mixture of human and mouse cells were separately aligned to the human and mouse genomes. Reads that aligned to both genomes were identified as alignments to homologous genomic regions and excluded from analysis. Reads that uniquely aligned to a single genome for each barcode were identified. Barcodes that primarily align to one genome were identified to be from that genome. Of 382 wells processed from the mixed cell sample, reads from 138 and 234 single-cell containing wells unambiguously aligned to human and mouse genomes respectively. Five well barcodes registered fewer than 25,000 alignments to either genome (Low Aligned Reads) and were excluded from further analysis. 5 of 382 wells from the mixed cell sample that gave rise to sequencing reads mapping to both species was used to calculate the multiple cell occupancy rate and partitioning ability of the system. In brief, 1.3% of barcodes show almost equal number of alignments to both genomes. In conclusion, the single cell occupancy and partitioning ability of the system is 98.7%, ie ~99% of wells were single-cell containing wells as shown in FIG. 17.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A method for performing analysis on single cells of interest, the method comprising:
   a. labeling at least one cell in a cell suspension with a first detectable label and a second detectable label, wherein the first detectable label identifies single cells while the second detectable label identifies cells of interest in the suspension;
   b. dispensing the suspension into a multi-well device using a robotic liquid dispensing system;
   c. generating a dispense map using a computer processor based on signals from the first detectable label and the second detectable label; and
   d. providing instructions, based on the dispense map, to the robotic liquid dispensing system to only dispense a reagent into wells containing the single cells of interest.

2. The method of claim 1, wherein the cell suspension comprises cells at a concentration such that, on average, one cell is present in the cell suspension.

3. The method of claim 1, wherein the detectable label comprises a cellular label.

4. The method of claim 3, wherein the cellular label comprises a stain, an antibody, nanomaterials, or any combination thereof.

5. The method of claim 1, wherein the first detectable label is fluorescent at a first wavelength and the second detectable label is fluorescent at a second wavelength.

6. The method of claim 1, wherein the multi-well device comprises at least 75 wells.

7. The method of claim 6, wherein said at least 75 wells is at least 150 wells.

8. The method of claim 1, wherein the robotic liquid dispensing system comprises a plurality of fluidic dispensing channels, wherein the channels are configured to move between a source container with the cell suspension or the reagent and the multi-well device.

9. The method of claim 1, wherein the reagent is selected from the group consisting of: a cell culture component, a cell differentiation reagent, a cell surface marker, an antibody, a nanomaterial, a cell lysis reagent, a drug, a nucleic acid, a lipid, a carbohydrate and a protein and combinations thereof.

10. A method for performing analysis on single cells of interest, the method comprising:
    a. labeling at least one cell in a cell suspension with a first detectable label, wherein the first detectable label identifies single cells;
    b. dispensing the suspension into a multi-well device using a robotic liquid dispensing system;
    c. labeling at least one cell in the multi-well device with a second detectable label, wherein the second detectable label identifies cells of interest in the suspension;
    d. generating a dispense map using a computer processor based on signals from the first detectable label and the second detectable label; and
    e. providing instructions, based on the dispense map, to the robotic liquid dispensing system to only dispense a reagent into wells containing the single cells of interest.

11. The method of claim 10, wherein the cell suspension comprises cells at a concentration such that, on average, one cell is present in the cell suspension.

12. The method of claim 10, wherein the detectable label comprises a cellular label.

13. The method of claim 12, wherein the cellular label comprises a stain, an antibody, nanomaterials, or any combination thereof.

14. The method of claim 10, wherein the first detectable label is fluorescent at a first wavelength and the second detectable label is fluorescent at a second wavelength.

15. The method of claim 10, wherein the multi-well device comprises at least 75 wells.

16. The method of claim 12, wherein said at least 75 wells is at least 150 wells.

17. The method of claim 10, wherein the robotic liquid dispensing system comprises a plurality of fluidic dispensing channels, wherein the channels are configured to move between a source container with the cell suspension or the reagent and the multi-well device.

18. The method of claim 10, wherein the reagent is selected from the group consisting of: a cell culture component, a cell differentiation reagent, a cell surface marker, an antibody, a nanomaterial, a cell lysis reagent, a drug, a nucleic acid, a lipid, a carbohydrate and a protein and combinations thereof.

* * * * *

UNITED STATES PATENT AND TRADEMARK OFFICE
CERTIFICATE OF CORRECTION

PATENT NO. : 11,125,752 B2
APPLICATION NO. : 16/834569
DATED : September 21, 2021
INVENTOR(S) : Alain-Albert Mir et al.

Page 1 of 1

It is certified that error appears in the above-identified patent and that said Letters Patent is hereby corrected as shown below:

In the Specification

Please replace "PSNEXTPTS" with -- P5NEXTPT5 -- (Column 25, Line 56).

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*